(12) United States Patent
Suckow et al.

US008778362B2

(10) Patent No.: US 8,778,362 B2
(45) Date of Patent: Jul. 15, 2014

(54) ANTI-TUMOR/CANCER HETEROLOGOUS ACELLULAR COLLAGENOUS PREPARATIONS AND USES THEREOF

(75) Inventors: Mark A. Suckow, Granger, IN (US); Michael C. Hiles, Lafayette, IN (US)

(73) Assignees: University of Notre Dame, Notre Dame, IN (US); Cook Biotech, West Lafayette, IN (US)

( * ) Notice: Subject to any disclaimer, the term of this patent is extended or adjusted under 35 U.S.C. 154(b) by 526 days.

(21) Appl. No.: 12/880,936

(22) Filed: Sep. 13, 2010

(65) Prior Publication Data
US 2012/0064163 A1 Mar. 15, 2012

Related U.S. Application Data

(63) Continuation-in-part of application No. 11/875,698, filed on Oct. 19, 2007, which is a continuation-in-part of application No. 11/583,771, filed on Oct. 20, 2006.

(60) Provisional application No. 60/730,379, filed on Oct. 27, 2005.

(51) Int. Cl.
A61K 9/00 (2006.01)
A61K 9/14 (2006.01)
A61K 9/70 (2006.01)

(52) U.S. Cl.
USPC ........ 424/277.1; 424/423; 424/443; 424/484; 424/489

(58) Field of Classification Search
None
See application file for complete search history.

(56) References Cited

U.S. PATENT DOCUMENTS

| | | |
|---|---|---|
| 2,172,903 A | 9/1939 | Charping |
| 3,346,401 A | 10/1967 | Barat et al. |
| 3,562,820 A | 2/1971 | Braun |
| 3,810,473 A | 5/1974 | Cruz, Jr. et al. |
| 4,502,159 A | 3/1985 | Woodroof et al. |
| 4,578,067 A | 3/1986 | Cruz, Jr. et al. |
| 4,902,508 A | 2/1990 | Badylak et al. |
| 4,956,178 A | 9/1990 | Badylak et al. |
| 5,028,695 A | 7/1991 | Eckmayer et al. |
| 5,275,826 A | 1/1994 | Badylak et al. |
| 5,281,422 A | 1/1994 | Badylak et al. |
| 5,336,616 A | 8/1994 | Livesey et al. |
| 5,352,463 A | 10/1994 | Badylak et al. |
| 5,372,821 A | 12/1994 | Badylak et al. |
| 5,437,287 A | 8/1995 | Phillips et al. |
| 5,460,962 A | 10/1995 | Kemp |
| 5,480,424 A | 1/1996 | Cox |
| 5,507,810 A | 4/1996 | Prewett et al. |
| 5,554,389 A | 9/1996 | Badylak et al. |
| 5,695,998 A * | 12/1997 | Badylak et al. ............... 435/391 |
| 5,733,337 A | 3/1998 | Carr, Jr. et al. |
| 5,782,914 A | 7/1998 | Schankereli |
| 6,156,305 A | 12/2000 | Brauker et al. |
| 6,206,931 B1 | 3/2001 | Cook et al. |
| 6,207,147 B1 | 3/2001 | Hiserodt et al. |
| 6,218,166 B1 | 4/2001 | Ravindranath et al. |
| 6,264,992 B1 | 7/2001 | Voytik-Harbin et al. |
| 6,277,368 B1 | 8/2001 | Hiserodt et al. |
| 6,403,104 B1 | 6/2002 | Berd et al. |
| 6,406,689 B1 | 6/2002 | Falkenberg et al. |
| 6,451,971 B1 | 9/2002 | Akiyama et al. |
| 6,548,066 B1 | 4/2003 | Michaeli et al. |
| 6,699,483 B1 | 3/2004 | Dalgeish et al. |
| 7,015,205 B1 | 3/2006 | Wallack et al. |
| 7,090,853 B2 | 8/2006 | Kapp et al. |
| 7,175,652 B2 | 2/2007 | Cook et al. |
| 7,550,004 B2 | 6/2009 | Bahler et al. |
| 7,575,926 B1 * | 8/2009 | Hurst et al. ................... 435/374 |
| 7,795,027 B2 | 9/2010 | Hiles |
| 2001/0006631 A1 | 7/2001 | Hiserodt et al. |
| 2003/0206901 A1 * | 11/2003 | Chen .......................... 424/140.1 |

(Continued)

FOREIGN PATENT DOCUMENTS

| | | |
|---|---|---|
| WO | WO 97/36495 A1 | 10/1997 |
| WO | WO 03/100034 A2 | 12/2003 |
| WO | 2005/023321 A2 | 3/2005 |
| WO | 2008/051852 | 5/2008 |

OTHER PUBLICATIONS

Wheeler, Salud p'ublica de M'exico, 1997, vol. 39, pp. 283-287.*
Suckow et al, Anticancer Research, 2008, vol. 28, pp. 2529-2534.*

(Continued)

*Primary Examiner* — Karen Canella
(74) *Attorney, Agent, or Firm* — Husch Blackwell LLP; Denise L. Mayfield

(57) ABSTRACT

Disclosed are mammalian tumor and/or cancer cell conditioned substrate preparations having tumor inhibiting activity. In some embodiments, the mammalian tumor and/or cancer cell conditioned substrate preparations are essentially free of cellular components. These preparations comprise a conditioned heterologous acellular collagenous tissue preparation, and may be prepared using a mammalian extracellular matrix substrate. The conditioned substrates include many different anti-tumor and/or anti-cancer biomolecules, such as that population of anti-tumor biomolecules that are secreted and/or produced by mammalian tumor and/or cancer cells as they grow on a substrate, thus imparting the anti-tumor and/or anti-cancer properties to the conditioned substrates of the invention. The present disclosure also provides methods for preparing the mammalian tumor and/or cancer cell conditioned substrates, as well as methods for using the preparations to inhibit tumor growth, such as in a vaccine or wound dressing. Methods for inhibiting prostate tumors and melanoma with the described conditioned substrates are also described. The conditioned mammalian tumor and/or cancer cell substrate preparations are essentially free of viable and/or carcinogenic or invasive tumor and/or cancer cells. The conditioned substrates and substrate preparations include anti-tumor and anti-cancer properties that may be used in preparations and formulations for the treatment of cancer.

16 Claims, 5 Drawing Sheets

(56) References Cited

U.S. PATENT DOCUMENTS

| | | | |
|---|---|---|---|
| 2004/0013712 A1 | 1/2004 | Parma | |
| 2006/0099675 A1 | 5/2006 | Benard | |
| 2008/0254139 A1 | 10/2008 | Firestone | |
| 2008/0260800 A1* | 10/2008 | Suckow et al. | 424/425 |
| 2009/0248144 A1 | 10/2009 | Bahler et al. | |
| 2011/0135690 A1* | 6/2011 | Suckow | 424/277.1 |

OTHER PUBLICATIONS

Horacek et al, Journal of Cellular Physiology, 1992, vol. 151, pp. 180-189.*
Ansaloni et al (Journal of Investigative Surgery, 2007, vol. 20, pp. 237-241).*
Ghosh et al (Journal of Cellular Physiology, 2005, vol. 204, pp. 522-531).*
International Search Report, mailed Jul. 22, 2009 in PCT/US09/35062.
Ruozi, et al., Intact collagen and atelcollagen sponges: Characterization and ESEM observation, 2007, Materials Science and Engineering 27: 802-810.
Boring, CC et al., "Cancer Statisitcs," CA Cancer Journal for Clinicians, 1993, vol. 43, pp. 7-26.
Nomura, Abraham et al., "Serum Selenium and Subsequent Risk of Prostate Cancer," Cancer Epidemiology, Biomarkers & Prevention, Sep. 2000, vol. 9, pp. 883-887.
Brooks, James D., et al., "Plasma Selenium Level Before Diagnosis and the Risk of Prostate Cancer Development," Journal of Urology, Dec. 2001, vol. 166, pp. 2034-3038.
Hursting, Steven D., et al., "Types of Dietary Fat and the Incidence of Cancer at Five Sites," Preventative Medicine, (1990), vol. 19, pp. 242-253.
Gann, Peter H., et al., "Lower Prostate Cancer Risk in Men with Elevated Plasma Lycopene Levels: Results of a Prospective Analysis," JAMA, May 12, 1999, vol. 281, No. 18, p. 1682.
Gann, Peter H., et al., "Lower Prostate Cancer Risk in Men with Elevated Plasma Lycopene Levels: Results of a Prospective Analysis," Cancer Research, Mar. 15, 1999, vol. 15, pp. 1225-1230.
Tjoe, Benjamin A., et al., "Follow Up Evaluation of a Phase ii Prostate Cancer Vaccine Trial," The Prostate, 1999, vol. 40, pp. 125-129.
Tjoe, Benjamin A., et al., "Development of a Dendritic Cell Based Prostate Cancer Vaccine," Immunology Letters, 2000, vol. 74, pp. 873-893.
Gulley, et al., "Phase I Study of a Vaccine Using Recombinant Vaccina Virus Expressing PSA (rV-PSA) in patients with Metastatic Androgen—Independent Prostate Cancer," The Prostate, 2002, vol. 53, pp. 109-117.
Pollard, Morris and Luckert, Phyllis, "Transplantable Metastasizing Prostate Adenocarcinomas in Rats," Journal of the National Cancer Institute, Mar. 1975, vol. 54, No. 3, pp. 498-504.
Suckow, Mark, et al., "Heat-Labile Toxin Producing Isolates of *Pasteurella multocida* from Rabbits," Laboratory Animal Science, Apr. 1991, vol. 41, No. 2, pp. 151-156.
Ringler, Daniel et al., "Protection of Rabbits against Experimental Pasteurellosis by Vaccination with a Potassium Thiocyanate Extract of *Pasteurella multocida*," Infection and Immunity, Sep. 1985, vol. 49, No. 3, pp. 498-504.
Pollard, Morris and Luckert, Phyllis, "Production of Autochthonous Prostate Cancer in Lobund-Wistar Rats by Treatments with N-Nstroso-N-methylurea and Testosterone," JNCI, Aug. 1986, vol. 77, No. 2 pp. 583-587.
Pollard, Morris and Luckert, Phyllis, "Autochthonous Prostate Adenocarcinomas in Lobund-Wistar Rats; a Model System," The Prosate, 1987, vol. 11, pp. 219-227.
Pollard, Morris, "Lobund-Wistar Rat Model of Prostate Cancer in Man," The Prostate, 1998, vol. 37, pp. 1-4.
Hrouda, D., et al. "Mycobacterium vaccae (SRL172): a Potential Immunological Adjuvant Elevated in Rat Prostate Cancer," British Journal of Urology, 1998, vol. 82, pp. 870-876.
Hrouda, D., et al., "Allogenic Whole-Tumor Cell Vaccination in the Rat Model of Prostate Cancer," BJU International, 2000, vol. 86, pp. 742-748.
Griffith, Thomas S., et al., "Inhibition of Murine Prostate Tumor Growth and Activation of Immunoregulatory Cells with Recombinant Canarypox Viruses," Journal of the National Cancer Institute, Jul. 4, 2001, vol. 93, No. 13, pp. 998-1007.
Charles, Linda G., et al., "Antitumor Efficacy of Tumor Antigen Encoding Recombinant Poxvirus Immunization in Dunning Rat Prostate Cancer: Implications for Clinical Genetic Vaccine Development," World J. Urol., 2000, vol. 18, pp. 136.
Michael, Agniesla et al., "Delayed Disease Progression after Allogenic Cell Vaccination in Hormaone-Rsistant Prostate Cancer and Correlation with Immunologic Variables," Clin. Cancer Res., Jun. 15, 2005, vol. 11, No. 12, pp. 469-478.
Wang, Z. et al., "Lack of HLA Class i Antigen Expression by Melanoma Cells SK-Mel-33 Caused by Reading a Frameshift in $\beta$2-Microglobulin Messenger RNA," J. Clin. Invest., Feb. 1993, vol. 91, pp. 648-692.
Shekar, Malathy et al., "Breast Stroma Plays a Dominant Regulatory Role in Breast Epithelial Growth and Differentiation" : Implications for Tumor Development and Progression, Cancer Research, Feb. 15, 2001, vol. 61, pp. 1320-1326.
Cunha, Gerald R. et al., "Role of the Stromal Microenvironment in Carcinogenesis of the Prostate," Int. J. Cancer, 2003, vol. 107, pp. 1-10.
Wei, Yu-Quan, "Immunotherapy of Tumors with Vaccines based on Xenogeneic Homologous Molecules," Anti-Cancer Drugs, 2002, vol. 13, pp. 119-235.
Fong, Lawrence, et al., "Dendritic Cell-Based Xenoantigen Vaccination or Prostate Cancer Immunotherapy," The Journal of Immunology, 2001, vol. 167, pp. 7150-7156.
Srinivasan, Roopa, et al., "Tumor Antigens for Cancer Immunotherapy: Therapeutic Potential of Xenogenic DNA Vaccines," Journal of Translational Medicine, 2004, vol. 2, pp. 1-2.
Bergman, Phillip J. et al., "Long-Term Survival of Dogs with Advanced Malignant Melanoma after DNA Vaccination with Xenogeneic Human Tyrosinase: A Phase I Trial," Clinical Cancer Research, Apr. 2003, vol. 9, pp. 1284-1290.
He, Qiu-ming et al., "Inhibition of Tumor Growth with a Vaccine based on Xenogeneic Homologous Fibroblast Growth Factor Receptor-1 in Mice," Journal of Biological Chemistry, Jun. 13, 2003, vol. 24, pp. 21831-21836.
Fernandez-Acenero, M.J. et al., "Prognostic Influence of Tumor-Associated Eosinophilia Infiltrate and in Colorectal Carcinoma," Cancer, (2002) vol. 88, pp. 1544-1548.
Ohashi, Yusuke et al., "Significance of Tumor Associated Tissue Eosinophilia and Other Inflammatory Cell Infiltrate in Early Esophageal Squamous Cell Carcinoma," Anticancer Research, (2002), vol. 20, pp. 3025-33030.
Fubert-Harris, Paulette et al., "Inhibition of Prostate Cancer Cell Growth by Activated Eosinophils," The Prostate, (2003), vol. 57, pp. 165-175.
Aguzza, et al., "Pathogenesis of Prion Diseases: Current Status and Future Outlook," *Microbiology*, (2006), vol. 4, pp. 765-775.
Caughey, et al., "Prions and their Partners in Crime," *Nature*, (2006) vol. 44, pp. 803-810.
Edwards B.K., et. al., *J Natl Cancer Inst* (2005); 97(19):1407-27.
Greenlee RT, Harmon M.B., Murray T, Thun M., "Cancer Statistics," (2001), *CA Cancer J Clin*., (2001);51:15-36.
Simons J.W., Sacks N., *Urol. Oncol.*, (2006);24:419-424.
Fukino K, et al., *Cancer Res.*, (2004);64(20):7231-6.
Bissell MJ, et al., *J. Cell Sci. Suppl.*, (1987);8(3):327-43.
Matrisian LM, et al., *Cancer Res.*, (2001);61(9)3844-6.
Shekhar MP, et al., *Cancer Res.*, (2001);61(4):1320-6.
Tatenhorst L, et al. "Genes Assocoated with Fast Glioma Cell Migration in vitro and in vivo", Brain Pathol., (2005);15(1):46-54.
Moschella F, et al., *Oncol Res.*, (2003);14(3):133-45.
Brewer J.M., "How do Aluminum Adjuvants Work?" *Immunol Lett.*, (2006); 102(1):10-5.
Lindblad, EB., *Immunol Cell Biol.*, (2004);82(5):497-505.
Barr, TA, et. al., Vaccine, (2006); 24(17):3399-407.
Hodge, J.W., *Front Biosci.*, (2006); 11:788-803.

(56) References Cited

OTHER PUBLICATIONS

Knoll L.D., *Urology*, (2001);57:753-757.
Knoll L.D., *Urology*, (2002);59:758-761.
Mantovani F, et al., *Eur Urol.*, (2003);44:600-602.
O'Connor RC, Patel RV, Steinberg GD., *J Urology*, (2001);165:1995.
O'Connor RC, Hollowell CM, Steinberg GD., *Urology*, (2002);60:697x-697xii.
O'Connor, RC, Harding JN, Steinberg GD., *Urology*, (2002);60:906-909.
Paradiso M, et. al., *Arch Ital Urol. Androl.*, (2003);75:116-118.
Weiser AC, et al., *J. Urol*, (2003);170:1593-1595.
Oasis, Benbow M., "An Innovative Alternative Dressing for Chronic Wounds", *Br. J. Nurs.*, (2001);10:1489-1492.
Brown-Etris M, Cutshall WD, Hiles M.C., *Wounds*, (2002);14:150-166.
Schultz DJ, et al., *J. Am Coll. Surg.*, (2002); 194:541-543.
Suckow M.A., et al., *Journal of Investigative Surgery*, (1999); 12:277-287.
Badylak, S.F., *Small Intestinal Submucosa (SIS): A Biomaterial Conducive to Smart Tissue Remodeling, Tissue Engineering: Current Perspectives*, Bell E (ed). Burkhauser Publishers, Cambridge, MA., (1993), pp. 179-189.
Badylak, S.F., "The Extracellular Matrix as a Scaffold for Tissue Reconstruction", *Seminars in Cellular and Developmental Biology*, (2002); 13:377-383.
Suckow MA, Hodde JP, Wolters WR, Hiles MC., *J Wound Care*, (2005), 14:137-140.
Suckow MA, Hodde JP, Wolter WR, Hiles MC., "Surgical Repair of Experimental Achilles Tenotomy with Porcine Renal Capsule Material in a Rat Model" *J. Mater Sci. Mater. Med.*
Lantz, G.C., et al., *J. Invest. Surg.*, (1993), 6:297.
Badylak, S.F., Lantz, G., Coffey, A., and Geddes, L.A., *J. Surg. Res.*, (1989), 47:74.
Lantz, G.C., Badylak, S.F., Coffey, A.C., Geddes, L.A., Blevins, W.E., *J. Invest. Surg.*, (1990), 3:217.
Hodde, J.P., and Hiles, M.C., *Biotechnol. Bioeng.*, (2002), 79:211.
Pollard M, Suckow M.A., "Hormone-Refractory Prostate Cancer in the Lobund-Wistar Rat," *Experimental Biology and Medicine*, (2005), 230:520-526.
Suckow MA, Wolter WR, Pollard M., *Cancer Immunology and Immunotherapy*, (2005); 54:571-576.
Pollard M, Lucked P.H., *J. Natl. Cancer Inst.*, (1975); 54:643-49.
Badylak SF, Record R, Lindberg K, Hodde J, Park K., *Journal of Biomaterials Sciences Polymer Edition*, (1998); 9:863-878.
Hodde, JP., et al., *J. Surg. Res.*, (2004); 120: 189-194.
Culora GA, Ramsay AD, Theaker JM., *J. Clin. Pathol.*, (1996); 49:844-847.
McDevitt CA, Wildey GM, Cutrone RM., *J. Biomed. Mater. Res.*, (2003);67A:637-646.
Bello-DeOcampo D, Tindall D.J., "TGF-beta/Smad signaling in Prostate Cancer", *Curr. Drug Targets*, (2003);4:197-210.
Voytik-Harbin S.L., et al., *Tissue Eng.*, (1998);4:157-174.
Michael A., et al., *Clin, Cancer Res.* (2005); 11:4469-4478.
Pilla L, et al., *Cancer Immunol Immunother.*, (2006);55:958-968.
Berd D, et at, *J. Clin Oncol.*, (1997);15:2359-2370.
Petrovsky N., *Vaccine*, (2006);24 Suppl. 2:S2:26-9.
Bendandi, M. et al., *Leuk. Lymphoma.*, (2006);47:29-37.
Redfern C.H., et al. *J Clin Oncol.*, (2006);24:3107-12.
Totterman TH, Loskog A, Essand M., *BJU Int.*, (2005);96:728-735.
Moscilits S, Nilsson B, Mellstedt H., "Towards Therapeutic Vaccines for Colorectal Carcinoma: A Review of Clinical Trials" *Expert Rev. Vaccines*, (2005);4:329-350.
He X, Tsang TC, Zhang T, Luo P, Harris DT., *Vaccine*, (2004);23:1966-1972.
Wei Y, Sticca R.P., et al., *Int. J. Oncol.*, (2006);28:585-593.
Rousseau RF, et al., *Blood*, (2006);107:1332-1341.
Akhurst, Rosemary, *J. Clin. Invest.* (2002); 1533-1536.
Kenney RT, et al., *J. Infect. Dis.*, (2004);190:774-782.
Skountzou I, et al., *Vaccine*, (2006);24:6110-6119.
Glenn GM, Kenney R.T., *Curr. Topics Microbiol. Immunol.*, (2006);304:247-268.
Rechsteiner G, et al., *J. Immunol.*, (2005);174:2476-2480.
Huang C.M, et al., *Proteomics*, (2005);5:1013-1023.
Michael, et al., *Clin. Cancer Res.*, (2005);11:4469-4478.
Aguzzi et al., (2003), "Immune system and peripheral nerves in propagation of prions to CNS," *Br Med Bull.*, 2003;66:141-59.
Allman et al., (2001), "Xenogeneic extracellular matrix grafts elicit a TH2-restricted immune response," *Transplantation*, 71:1631-1640.
Arbel et al., (2003), "Generation of antibodies against prion protein in wild-type mice via helix 1 peptide immunization," *J Neuroimmunol.*, 144(1-2):38-45.
Baars et al., (2000), "Skin tests predict survival after autologous tumor cell vaccination in metastatic melanoma: experience in 81 patients," *Ann. Oncol.*, 11:965-970.
Banzhoff et al., (2003), "A new MF59-adjuvanted influenza vaccine enhances the immune response in the elderly with chronic diseases: results from an immunogenicity meta-analysis," *Gerontology*, 49(3):177-84.
Ben-Efraim et al., (2000), "Use of xenogenized (modified) tumor cells for treatment in experimental tumor and in human neoplasia," *Biomed & Pharmacotherapy*, 54:268-273.
Berd et al., (1990), "Treatment of metastatic melanoma with an autologous tumor-cell vaccine: clinical and immunologic results in 64 patients," *J. Clin. Oncol.*, 8:8158-1867.
Berraondo et al., (2007), "Eradication of large tumors in mice by a tritherapy targeting the innate, adaptive, and regulatory components of the immune system," *Cancer Res.*, 67:8847-8855.
Bodey et al., (2000), "Failure of cancer vaccines: the significant limitations of this approach to immunotherapy," *Anticancer Res.*, 20:2665-2676.
Brando et al., (2007), "Murine immune responses to liver-stage antigen 1 protein FMP011, a malaria vaccine candidate, delivered with adjuvant AS01B or AS02A," *Infect Immun.*, 75(2):838-45.
Burch et al., (2000), "Priming tissue-specific cellular immunity in a phase I trial of autologous dendritic cells for prostate cancer," *Clin. Cancer Res.*, 6:2175-2182.
Burch et al., (2004), "Immunotherapy (APC8015, Provenge) targeting prostatic acid phosphatase can induce durable remission of metastatic androgen-independent prostate cancer: a phase 2 trial," *Prostate*, 60:197-204.
Caglar et al., (2005), "Effect of monophosphoryl lipid A on antibody response to diphtheria toxin and its subunits," *APMIS*, 113(4):256-63.
Chang et al., (2000), "Antigen-Specific Cancer Immunotherapy Using a GM-CSF secreting allogeneic tumor cell-based vaccine," *Int. J. Cancer*, 86:725-730.
Chatterjee et al., (1994), "Idiotypic antibody immunotherapy of cancer," *Cancer Immunol. Immunother.*, 38:75-82.
Corman et al., (1998), "Recognition of prostate-specific antigenic peptide determinants by human CD4 and CD8 T cells," *Clin. Exp. Immunol.*, 114:166-172.
Correale et al., (1997), "In vitro generation of human cytotoxic T lymphocytes specific for peptides derived from prostate-specific antigen," *J. Natl. Cancer Inst. USA*, 89:293-300.
de Souza Matos et al., (2000), "Immunostimulatory effects of polar glycopeptidolipids of *Mycobacterium chelonae* for inactivated rabies vaccine," *Vaccine*, 18(20):2125-31.
Degruijl et al., (1999), "Cancer vaccine strategies get bigger and bigger," *Nature Medicine*, 5:1124-1125.
Denmeade et al., (2003), "Prostate specific antigen (PSA) does not affect growth of prostate cancer cells in vitro or prostate cancer xenografts in vivo," *Prostate*, 56:45-53.
Desai et al., (2000), "Immune response with biodegradable nanospheres and alum: studies in rabbits using staphylococcal enterotoxin B-toxoid," *J Microencapsul.*, 17(2):215-25.
Dillman et al., (1998), "Clinical experience with autologous tumor cell lines for patient-specific vaccine therapy in metastatic melanoma," *Cancer Biother, Radiopharm.*, 13:165-173.
Dillman et al., (2001), "Short-term cell lines from breast cancer for use as autologous tumor cell vaccines in the treatment of breast cancer," *Cancer Biotherapy & Radiopharmaceuticals*, 16:205-211.

(56) References Cited

OTHER PUBLICATIONS

Dols et al., (2003), "Vaccination of women with metastatic breast cancer using a costimulatory gene (CD80)-modified, HLA-A2 matched allogeneic, breast cancer cell line: clinical and immunological results," *Human Gene Therapy*. 14:1117-1123.
Donnelly, (2003), "Cancer vaccine targets leukemia," *Nature Medicine*, 9:1354-1356.
Eaton et al., (2002), "Allogeneic whole-cell vaccine: a phase I/II study in men with hormone-refractory prostate cancer," *British Journal of Urology*. 89:19-26.
Eldridge et al., (1991), "Biodegradable and biocompatible poly(DL-lactide-co-glycolide) microspheres as an adjuvant for staphylococcal enterotoxin B toxoid which enhances the level of toxin-neutralizing antibodies,"*Infect Immun*., 59(9):2978-86.
Enari et al., (2001), "Scrapie prion protein accumulation by scrapie-infected neuroblastoma cells abrogated by exposure to a prion protein antibody," *Proc Natl Acad Sci USA*, 98(16):9295-9.
Evans et al., (1999), "Vaccine therapy for cancer—fact or fiction?" *Q. J. Med*., 92:299-307.
Ezzell, (1995), "Cancer 'vaccines': an idea whose time has come?" *J. NIH Res*., 7:4-49.
Finn et al., (2002), "Prophylactic Cancer Vaccines," *Curr. Opin. Immunol*., 14:172-177.
Flick-Smith et al., (2002), "Mucosal or parenteral administration of microsphere-associated *Bacillus anthracis* protective antigen protects against anthrax infection in mice," *Infect Immun*., 70(4):2022-8.
Forni et al., (2000), "Immunoprevention of cancer," *Cancer Res*., 60:2571-2575.
Frost et al., (1975), "Tumor immunoprophylaxis in mice using glutaraldehyde-treated syngenic tumor cells," *Cancer Res*., 35:2646-2650.
Fuessel et al., (2006), "Vaccination with hormone-refractory prostate cancer patients with peptide cocktail-loaded dendritic cells: results of phase I clinical trial," *Prostate*, 66:811-821.
Gikh et al., (2003), "Polyclonal anti-PrP auto-antibodies induced with dimeric PrP interfere efficiently with PrPSc propagation in prion-infected cells," *J Biol Chem*., 278(20):18524-31.
Granziero et al., (1999), "Adoptive immunotherapy prevents prostate cancer in a transgenic animal model," *Eur. J. Immunol*., 29:1127-1138.
Griffiths et al., (1997), "Liposomally-encapsulated ricin toxoid vaccine delivered intratracheally elicits a good immune response and protects against a lethal pulmonary dose of ricin toxin," *Vaccine*, 15(17-18):1933-9.
Gu et al., (2002), "Substitution of porcine small intestinal submucosa for rabbit Achilles tendon, an experimental study," *Natl. Med. J. China*, 82:1279-1282 (Chinese language with English abstract).
Hahn et al., (2006), "Short-term dietary administration of celecoxib enhances the efficacy of tumor lysatepulsed dendritic cell vaccines in treating murine breast cancer," *Int. J. Cancer*, 118:2220-2231.
Hanan et al., (2001), "Antiaggregating antibody raised against human PrP 106-126 recognizes pathological and normal isoforms of the whole prion protein," *Cell Mol Neurobiol*., 21(6):693-703.
Hanan et al., (2001), "Immunomodu1ation of the human prion peptide 106-126 aggregation," *Biochem Biophys Res Commun*., 280(1):115-20.
Harada et al., (2003), "Prostate-specific antigen-derived epitopes capable of inducing cellular humoral responses in HLA-A24+ prostate cancer patients," *Prostate*, 57:152-159.
Hedlund et al., (2001), "Negligible adjuvant effect for antibody responses and frequent adverse events associated with IL-12 treatment in humans vaccinated with pneumococcal polysaccharide," *Vaccine*, 20(1-2)164-9.
Higgins et al., (1996), "MF59 adjuvant enhances the immunogenicity of influenza vaccine in both young and old mice," *Vaccine*, 14(6):478-84.
Horiguchi et al., (2002), "Screening of HLA-A24-restricted epitope peptides from prostate-specific membrane antigen that induces specific antitumor cytotoxic T lymphocytes," *Clin. Cancer Res*., 8:3885-3892.
Jaganathan et al., (2006), "Strong systemic and mucosal immune responses to surface-modified PLGA microspheres containing recombinant hepatitis B antigen administered intranasally," *Vaccine*, 24(19):4201-11.
Jager et al., (2003), "Antigen-specific immunotherapy and cancer vaccines," *Intl. J. Cancer*, 106:817-820.
Jarvinen et al., (2000), "Intranasal vaccination of New Zealand white rabbits against pasteurellosis using alginate-encapsulated *Pasteurella multocida* toxin and potassium thiocyanate extract," *Comparative Medicine*, 50:263-269.
Jocham et al., (2004), "Adjuvant autologous renal tumour cell vaccine and risk of tumour progression in patients with renal-cell carcinoma after radical neprectomy: phase III, randomised controlled trial," *Lancet*, 363:594-599.
Kende et al., (2006), "Enhancement of intranasal vaccination in mice with deglycosylated chain A ricin by LTR72, a novel mucosal adjuvant," *Vaccine*, 15;24(12):2213-21.
Kenney et al., (1999), "Protective immunity using recombinant human IL-12 and alum as adjuvants in a primate model of cutaneous leishmaniasis," *J Immunol*., 163(8):4481-8.
Kobayashi et al., (2003), "Identification of naturally processed helper T-cell epitopes from prostate-specific membrane antigen using peptide-based in vitro stimulation," *Clin. Cancer Res*., 9:5386-5393.
Kochenderfer et al., (2007), "Maximizing CD8+ T cell responses elicited by peptide vaccines containing CpG oligodeoxynucleotides," *Clin. Immunol*., 124:119-130.
Koller et al., (2002), "Induction of antibodies against murine full-length prion protein in wild-type mice," *J. Neuroimmunol*., I32(1-2):113-6.
Komenaka et al., (2004), "Immunotherapy for melanoma," *Clinics in Dermatology*, 22:251-265.
Langermans et al., (2005), "Effect of adjuvant on reactogenicity and long-term immunogenicity of the malaria Vaccine ICC-1132 in macaques," *Vaccine*, 23(41):4935-43.
Lee et al., (1999), "Increased vaccine-specific T cell frequency after peptide-based vaccination correlates with increased susceptibility to in vitro stimulation but does not lead to tumor regression," *J. Immunol*., 163:6292-6300.
Levesque et al., (2006), "Association between immunogenicity and adsorption of a recombinant *Streptococcus pneumoniae* vaccine antigen by an aluminum adjuvant," *Hum Vaccin*., 2(2):74-7.
Lord et al., (2007), "Low dose metronomic oral cyclophosphamide for hormone resistant prostate cancer: a phase II study," *J. Urology*, 177:2136-2140.
Lu et al., (2002), "Recognition of prostate tumor cells by cytotoxic T lymphocytes specific for prostate-specific membrane antigen," *Cancer Res*., 62:5807-5812.
Lubaroff et al., (2006), "Decreased cytotoxic T cell activity generated by co-administration of PSA vaccine and CpG ODN is associated with increased tumor protection in a mouse model of prostate cancer," *Vaccine*, 24:6155-6162.
Martin, (1997), "Development of an adjuvant to enhance the immune response to influenza vaccine in the elderly," *Biologicals*, 25(2):209-131.
Matsueda et al., (2005), "Identification of peptide vaccine candidates for prostate cancer patients with HLS-A3 super-type alleles," *Clin. Cancer Res*., 11:6933-6943.
McNeel et al., (2001), "Identification of T helper epitopes from prostatic acid phosphatae," *Cancer Res*., 61:5161-5167.
Mendez et al., (2003), "Coinjection with CpG-containing immunostimulatory oligodeoxynucleotides reduces the pathogenicity of a live vaccine against cutaneous Leishmaniasis but maintains its potency and durability,"*Infect Immun*. 71(9):5121-9.
Miller et al., (2006), "The role of melatonin in immuno-enhancement: potential application in cancer," *Int. J. Exp. Path*., 87:81-87.
Moody et al., (1994), "Interleukin-2 transfected prostate cancer cells generate a local antitumor effect in vivo," *Prostate*, 24:244-251.
Mullen et al., (2006), "Enhancement of functional antibody responses to AMA1-C1/Alhydrogel, a *Plasmodium falciparum* malaria vaccine, with CpG oligodeoxynucleotide," *Vaccine*, 24(14):2497-505.

(56) References Cited

OTHER PUBLICATIONS

Ochsenbein et al., (1999), "Immune surveillance against a solid tumor fails because of immunological ignorance," *Proc. Natl. Acad. Sci. USA*, 96:2233-2238.
Okaji et al., (2004), "Vaccination with autologous endothelium inhibits angiogenesis and metastasis of colon cancer through autoimmunity," *Cancer Science*, 95:85-90.
Palese, (2006), "Making better influenza virus vaccines?" *Emerg Infect Dis.*, 12(1):61-5.
Peng et al., (2006), "Novel vaccines for the treatment of chronic HBV infection based on mycobacterial heat shock protein 70," *Vaccin*, 24(7):887-96.
Peretz et al., (2001), "Antibodies inhibit prion propagation and clear cell cultures of prion infectivity," *Nature*, 412(6848):739-43.
Peters et al., (1979), "Preparation of immunotherapeutic autologous tumor cell vaccines from solid tumors," *Cancer Res.*, 39:1353-1360.
Petrik et al., (2007), "Aluminum adjuvant linked to Gulf War illness induces motor neuron death in mice," *Neuromolecular Med.*, 9:83-100.
Pimenta et al., (2006), "Intranasal immunization with the cholera toxin B subunit-pneumococcal surface antigen A fusion protein induces protection against colonization with *Streptococcus pneumoniae* and has negligible impact on the nasopharyngeal and oral microbiota of mice," *Infect Immun.*, 74(8):4939-44.
Pollard et al., (2006), "Dietary prevention of hormone refracetory prostate cancer in Lobund-Wistar rats: a review of studies in relevant animal model," *Compo Med.*, 56:461-467.
Polymenidou et al., (2004), "Humoral immune response to native eukaryotic prion protein correlates with antiprion protection," *Proc Natl Acad Sci U S A*, 101 Suppl 2:14670-6.
Qin et al., (2004), "CpG ODN enhances immunization effects of hepatitis B vaccine in aged mice," *Cell Mol.Immunol.*, 1(2):148-52.
Rosado-Vallado et al., (2005), "Aluminium phosphate potentiates the efficacy of DNA vaccines against *Leishmania mexicana*," *Vaccine*, 23(46-47):5372-9.
Rosset et al., (2004), "Breaking immune tolerance to the prion protein using prion protein peptides plus oligodeoxynucleotide-CpG in mice," *J Immunol.*, 172(9):5168-74.
Sabirov et al., (2006), "Intranasal vaccination of neonatal mice with polysaccharide conjugate vaccine for protection against pneumococcal otitis media," *Vaccine*, 24(27-28):5584-92.
Sanderson et al., (1974), "The induction of tumour immunity in mice using glutaraldehyde-treated tumor cells," *Nature*, 248:690-691.
Schwarz et al., (2004), "Immunisation with a synthetic prion protein-derived peptide prolongs survival times of mice orally exposed to the scrapie agent," *Neurosci Lett.*, 350(3):187-9.
Segura-Velazquez et al., (2006), "A novel synthetic adjuvant effectively enhances the immunogenicity of the influenza vaccine," *Vaccine*, 24(8):1073-80.
Sen et al., (2006), "Immunization of aged mice with a pneumococcal conjugate vaccine combined with an unmethylated CpG-containing oligodeoxynucleotide restores defective immunoglobulin G antipolysaccharide responses and specific CD4+-T-cell priming to young adult levels," *Infect Immun.*, 74(4):2177-86.
Sigurdsson et al., (2002), "Immunization delays the onset of prion disease in mice," *Am J Pathol.*, 161(1):13-7.
Simons et al., (1999), "Induction of immunity to prostate cancer antigens: results of a clnical trial of vaccination with irradiated autologous prostate tumor cells engineered to secrete granulocyte-macrophage colony-stimulating factor using ex vivo gene transfer," *Cancer Res.*, 59:5160-5168.
Simons et al., (2002), "Phase II trials of a GM-CSF genetransduced prostate cancer cell line vaccine (GVAX) in hormone refractory prostate cancer," *Proc. Am. Soc. Clin. Oncol.*, 21: 183a (Abstract 729).
Singh et al., (1992), "Stroma is critical for preventing or permitting immunological destruction of antigenic cancer cells," *J. Exp. Med.*, 175:139-146.
Small et al., (2000), "Immunotherapy of hormone-refractory prostate cancer with antigen-loaded dendritic cells," *J. Clin. Oncol.*, 18:3894-3903.
Small et al., (2005), "Results of a placebo-controlled phase III trial of immunotherapy with APC8015 for patients with homrone refractory prostate cancer (HRPC)," *Proc. Am. Soc. Clin. Oncol.*, 23(16S):378S (Abstract 4500).
Souan et al., (2001), "Modulation of proteinase-K resistant prion protein by prion peptide immunization," *Eur J Immunol.*, 31(8):2338-46.
Stack et al., (1982), "Autologous X-irradiated tumor cells and percutaneous BCG in operable lung cancer," *Thorax*, 37:599-593.
Stewart et al., (2006), "Pre-clinical evaluation of new adjuvant formulations to improve the immunogenicity of the malaria vaccine RTS,S/AS02A," *Vaccine*, 24(42-43):6483-92.
Suckow et al., (2007), "Prevention of human PC-346C prostate cancer growth in mice by xenogeneic tissue vaccine," *Cancer Immunol. Immunother.*, 56:1275-1283.
Suckow et al., (2007), "Surgical Repair of Experimental Achilles Tenotomy with Porcine renal capsule material in a rat model," *J. Mater. Sci. Mater. Med.*, 18:1105-1110.
Suckow et al., (2007), "Tissue vaccines for cancer," *Expert. Rev. Vacc.*, 6:925-937.
Sugai et al., (2005), "A CpG-containing oligodeoxynucleotide as an efficient adjuvant counterbalancing the Th1/Th2 immune response in diphtheria-tetanus-pertussis vaccine," *Vaccine*, 23(46-47):5450-6.
Süli et al., (2004), "Experimental squalene adjuvant. I. Preparation and testing of its effectiveness," *Vaccine*, 22(25-26):3464-9.
Sung et al., (2006), "HBV-ISS (Dynavax)," *Curr Opin Mol Ther.*, 8(2):150-5.
Teir et al., (1957), "Effects of intraperitoneally injected suspension of roetgen irradiated and non-irradiated tumor tissue on the growth of homologous tissue," *Acta Pathol. Microbiol. Scand.*, 40:273-282.
Theeten et al., (2005), "Effects of lowering the aluminium content of a dTpa vaccine on its immunogenicity and reactogenicity when given as a booster to adolescents," *Vaccine*, 10;23(12):1515-21.
Vermorken et al., (1999), "Active specific immunotherapy for stage II and stage III human colon cancer: a randomized trial," *Lancet*, 353:345-350.
Vieweg et al., (1994), "Immunotherapy of prostate cancer in the Dunning rate model: use of cytokine gene modified tumor vaccines," *Cancer Res.*, 54:1760-1765.
Vitetta et al., (2006), "A pilot clinical trial of a recombinant ricin vaccine in normal humans," *Proc Natl Acad Sci USA*, 103(7):2268-73.
Wilson et al., (1997), "Human prostate tumor angiogenesis in nude mice: metalloprotease and plasminogen activator activities during tumor growth and neovascularization of subcutaneously injected matrigel impregnated with human prostate tumor cells," *Anatomical Record*, 249:63-73.
Xue et al., (1997), "Induction of human cytotoxic T lymphocytes specific for prostate-specific antigen," *Prostate*, 30:73-78.
Zhang et al., (2003), "Dendritic cells transfected with interleukin-12 and pulsed with tumor extract inhibit growth of murine prostatic carcinoma in vivo," *Prostate*, 55:292-298.
Written Opinion for International Application No. PCT/US2007/081962.
International Search Report for International Application No. PCT/US2007/081962.
International Search Report for corresponding Application No. PCT/US2011/051159 dated Feb. 17, 2012.
International Preliminary Report on Patentability for corresponding Application No. PCT/US2011/051159 dated Mar. 28, 2013.

\* cited by examiner

ANTI-TUMOR/CANCER HETEROLOGOUS ACELLULAR COLLAGENOUS PREPARATIONS AND USES THEREOF

This application is a continuation in part of U.S. patent application Ser. No. 11/875,698 filed Oct. 19, 2007. U.S. patent application Ser. No. 11/875,698 is a continuation-in-part of U.S. patent application Ser. No. 11/583,771, filed Oct. 20, 2006. U.S. Application patent application Ser. No. 11/583,771 is a non-provisional of provisional U.S. Patent Application 60/730,379 filed Oct. 27, 2005. Priority to all previously filed applications recited here is claimed for the present application Ser. No. 11/880,936.

STATEMENT OF JOINT RESEARCH AGREEMENT

In compliance with 37 C.F.R. §1.71(g) (1), disclosure is herein made that the claimed invention was made pursuant to a Joint Research Agreement as defined in 35 U.S.C. 103 (c) (3), that was in effect on or before the date the claimed invention was made, and as a result of activities undertaken within the scope of the Joint Research Agreement, by or on the behalf of the University of Notre Dame and Cook Biotech, Inc. (West Lafayette, Ind.).

The present invention relates generally to the field of vaccines, and more particularly to anti-tumor and anti-cancer vaccines and materials that include anti-tumor and/or anti-cancer biomaterials. The present invention also provides substrate materials that have been exposed to tumor and/or cancer cells to provide a conditioned substrate (e.g., extracellular matrix (ECM)) useful in vaccine preparation.

BACKGROUND OF THE INVENTION

There is a great interest in therapeutic and prophylactic cancer vaccines. A variety of methods have been examined. For example, vaccines derived from whole cells have been examined and found to have a larger number of antigens, and reported to have met with some success. Tissue vaccines are derived from tumor material harvested directly from tumor-bearing individuals, and contain not only antigens associated with neoplastic cells, but also a menu of antigens associated with the tumor connective tissue and extracellular matrix.

A material known by the acronym SIS, comprised of an extracellular matrix material derived from porcine small intestinal submucosa, has been described as a material useful as a tissue scaffold. (Cook Biotech Inc., West Lafayette, Ind.).

By way of further background, a variety of extracellular matrix materials have been proposed for use in medical grafting, cell culture, and other related applications. For instance, medical grafts and cell culture materials containing submucosa derived from small intestine, stomach or urinary bladder tissues have been proposed. (See, e.g., U.S. Pat. Nos. 4,902,508, 4,956,178, 5,281,422, 5,554,389, 6,099,567 and 6,206,931.) In addition, Cook Biotech Inc. (West Lafayette, Ind.), currently manufactures a variety of medical products based upon small intestinal submucosa under the trademarks SURGISIS®, STRATASIS® and OASIS®.

Medical materials derived from liver basement membrane have also been proposed, for example in U.S. Pat. No. 6,379,710. As well, ECM materials derived from amnion (see, e.g., U.S. Pat. Nos. 4,361,552 and 6,576,618) and from renal capsule membrane (see, e.g., WO003002165) have been proposed for medical and/or cell culture applications.

Some investigators have reported that small intestinal submucosa (SIS) material has an improved biocompatibility that makes it a useful tissue scaffolding material. (Woods, et al., (2004), Biomaterials, 25 (3):515-525.) In Woods, it is hypothesized that the human umbilical vein endothelial cells cultured on SIS (HUVEC) deposited human basement membrane proteins to create what was termed a "conditioned" SIS (c-SIS). The surface properties of the c-SIS were hypothesized to be changed in such a way that, upon re-seeding of human umbilical vein endothelial cells on the c-SIS substrate, the cells exhibited enhanced organization of cellular junctures and an increase in metabolic activity, compared to HUVEC cells cultured on a native, non-conditioned SIS (n-SIS) substrate. The HUVEC cells cultured on c-SIS were reported to release lower amounts of pro-inflammatory prostaglandin $PGI_2$ into the media, compared to HUVEC grown on n-SIS substrate. These effects were concluded to provide an SIS with improved properties as a tissue scaffolding material.

One group of researchers describe a conditioned cell culture media prepared from a culture of non-cancerous, non-tumor elasmobrach fish immune cells (i.e., cells obtained from epigonal organ or Leydig organ of elasmobrach fishes (e.g., sharks, skates, and rays)), and report the media to demonstrate anti-tumor activity (U.S. Pat. No. 7,309,501). The non-tumorous, non-cancerous fish immune cells are described as having released immune substances into the media of these cultures. These preparations do not describe the use of cells other than non-tumor, non-cancerous fish immune cells. Further, these preparations did not involve or reference the growth of cells on an extracellular matrix.

Carcinoma cells have been described as depositing fibrinogen. Fibrinogen is not converted to fibrin in the tumor stroma. The microenvironment of a tumor is composed of an amalgam of secreted soluble factors, solid material and tumor cells. Secreted soluble factors include chemokines such as CXCR-4 and CXCL-2, matrix altering enzymes such as matrix metalloproteinases (MMPs), protease inhibitors, and growth factors (e.g., vascular endothelial growth factor (VEGF)), all of which are stored in the surrounding ECM and released when required by the tumor cells (via protease-mediated degradation of the ECM). The surrounding ECM itself, which is composed of the interstitial matrix and basement membrane, constitutes the noncellular solid material, which is critical in the anchorage and migration of malignant cancer cells. (Alphonso, et al. (2009), Neoplasia, 11:1264-1271).

Cancer cells have been described as producing proteases (e.g., matrix metalloproteases, elastase, cathepsin-L) that remodel the ECM associated with a tumor. (Sund, et al., (2009), Cancer Metastasis Rev., 28:177-183). This remodeling leads to the release of substances sequestered in the ECM, as well as bioactive cleavage fragments from ECM proteins, such as collagen and proteoglycans. Sequestered substances which may be released into the tumor ECM include VEGF, which further influences tumor progression. Cancer cells also interact with the microenvironment through the release of soluble factors and through cell-matrix interactions. Examples of secretions or by-products include cadhereins, integrins, cytokines (IL-1, IL-6, IL-8, TNF-α, PDGF, EGF and TGF-β). Additional secreted molecules include endothelins, plasmin and uPA. (Zigrino, et al. (2005), Biochimie, 87:321-328).

Human breast cancer cells are shown to synthesize, secrete and deposit fibrinogen into the ECM. (Rybarczyk, et al. (2000), Cancer Res., 60: 2033-2039). Prostate cancer cells, in particular, have been reported to secrete bFGF, PDGF and TNF-α. (Kaminski, et al. (2006), Expert Opin. Ther. Targets, 14, 77-94). These and other products synthesized by various types of cancer cells have been described to contribute to the growth/spreading of cancer cells. However, it remains unknown whether tumor/cancer cell secretions and/or by-products demonstrate any anti-tumor and/or anti-cancer activities.

A need continues to exist in the medical arts for improved anti-cancer/anti-tumor preparations. In particular, improved preparations that are essentially cell free (acellular) that posses a tumor and/or cancer inhibiting activity continue to be pursued in the quest for improved anti-cancer and anti-tumor pharmaceuticals and vaccines. Improved tools for treatment and containment of cancer and tumor growth remain to be developed, and present the promise of a new generation of vaccines.

SUMMARY OF THE INVENTION

The present invention satisfies the above need in the art among many others. Various embodiments of the present invention are directed to a tumor inhibiting conditioned preparation comprising a conditioned heterologous acellular collagenous material substrate and anti-tumor, anti-cancer or combination of anti-tumor and anti-cancer biomolecules, wherein tumor and/or cancer cells have been cultured on said preparation under conditions suitable for growth of said cells on said substrate. The tumor and/or cancer cells can include melanoma cells or prostate tumor cells, among others. In certain embodiments, the prostate tumor cells are human prostate cells. In some embodiments of the invention, the substrate is an extracellular matrix. In others, the substrate is essentially free of tumor and/or cancer cells.

In other embodiments of the invention, a method for inhibiting tumor regrowth in a patient is provided comprising: preparing the tumor inhibiting conditioned preparation of the present invention; applying said preparation to a site in a patient at which a tumor or cancerous cell growth has been removed; and inhibiting tumor regrowth at said site. In certain embodiments of the invention, the method further comprises the step of processing the preparation to remove cellular material without degradation to the collagen components of the preparation. This processing step can comprise treatment with a chemical compound, sonication or freezing the preparation and thawing the preparation, among others.

Certain embodiments of the present invention are directed to a vaccine comprising the tumor inhibiting conditioned preparation of the present invention.

In other embodiments, a tumor wound dressing material is provided comprising the tumor inhibiting conditioned preparation of the present invention.

Still other embodiments of the invention provide an injectable preparation suitable for subcutaneous administration to a patient as a vaccine comprising the substrate of the present invention in a particulate form in a pharmaceutically acceptable carrier.

Further embodiments of the invention are directed to a method of preparing a tumor and/or cancer conditioned extracellular matrix substrate comprising: culturing tumor and/or cancer mammalian cells on a substrate suitable for the culture of said cells for a period of time and under conditions suitable for growth of said cells on said substrate so as to provide a conditioned substrate; and processing said conditioned substrate to remove cellular components from said culture.

BRIEF DESCRIPTION OF THE FIGURES

The invention may be more completely understood in consideration of the following detailed description of various embodiments of the invention in connection with the accompanying Figures.

FIG. 4 is a bar chart summarizing a study wherein animals were vaccinated with either media (MEM); a vaccine made of glutaraldehyde-fixed tumor cells (GFT); or with a vaccine composed of tumor cells grown on SIS and then lysed with potassium thiocyanate (TC/ECM). Animals were euthanized 21 days after challenge and tumors weighed. The results demonstrate an anti-tumor immunity in animals treated with the GFT, as compared to controls. Mean tumor weight for mice in the GFT vaccination group was significantly lower than those for the MEM groups ($P<0.005$), and was lower than the mean tumor weight for the TC/ECM vaccination group ($P<0.05$). Mean tumor weight for mice in the TC/ECM vaccination group was significantly lower ($P<0.01$) than mean tumor weights of the MEM control group.

DETAILED DESCRIPTION

Figure 1:
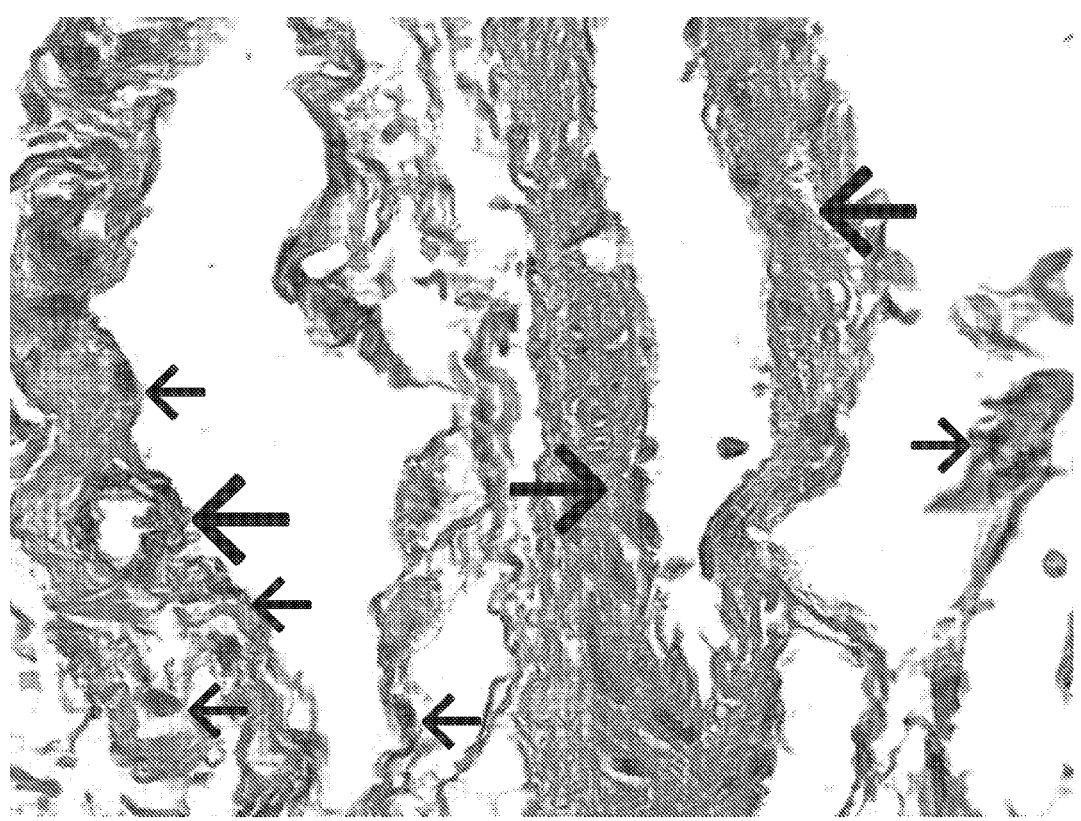
FIG. 1 is a micrograph of tissue showing tumor cells grown on SIS, an extracellular matrix material derived from porcine small intestinal submucosa, in accordance with one embodiment of the present invention.

The present invention provides unique anti-tumor and/or anti-cancer conditioned preparations and materials that comprise a combination of potent tumor inhibiting and/or cancer inhibiting biomolecules with a heterologous acellular collagenous material. These tumor and/or cancer inhibiting biomolecules may be further described as a group or concentration of a group of specific biomolecules, or a unique combination, concentration, or ratio of specific anti-tumor and/or anti-cancer biomolecules, that demonstrate a physiologically detectable anti-tumor and/or anti-cancer cell activity. For example, cytokines such as VEGF and EMAP-II have been reported to be produced in varying amounts by tumors, and to have different effects on tumor neovasculature. Thus, it is envisioned that when a tumor cell and/or cancer cell conditioned, heterologous, acellular collagenous matrix of the present invention is provided and/or placed in a physiological environment, such as in or on the body or at a specific tissue site, or is injected, the anti-tumor and/or anti-cancer cell conditioned heterologous, acellular, collagenous matrix will interact with the microenvironment of the tissue and/or body site, or specific population of cells, to elicit a physiologically demonstrable tumor inhibiting, cancer cell inhibiting and/or observable and/or quantifiable tumor/cancer cell stasis response (no and/or reduced cancer and/or tumor cell growth or replication). These properties render the preparations and/or formulations of the present invention suitable for use at a surgical site where a tumor and/or cancerous growth has been removed and/or reduced in size, as well as in virtually any in vivo environment (e.g., injected into the animal as a vaccine preparation), where a tumor inhibiting, cancer cell inhibiting and/or cancer cell stasis response (no and/or reduced cancer cell and/or tumor growth), is desired or otherwise is needed in the clinical management or treatment of a patient.

The anti-tumor and/or anti-cancer biomolecule conditioning of a substrate (e.g., the heterologous, acellular collagenous substrate material) as described herein, results in an inhibiting combination and/or ratio of tumor and/or cancer cell inhibiting biomolecules within and/or on the substrate material. For example, and in some embodiments, secretion and/or release of anti-tumor and/or anti-cancer biomolecules onto and in the heterologous acellular collagenous material substrate provides a conditioned anti-tumor and/or anti-cancer material that may be used to inhibit and/or arrest the growth or regrowth of a tumor or cancer cells (e.g., malignant melanoma) in vivo at the site where the conditioned material/substrate is placed.

Thus, in a general and overall sense, the present invention provides a composition that comprises an anti-tumor and/or anti-cancer conditioned substrate preparation, the substrate being conditioned ("c") by the deposition of one or more anti-tumor and/or anti-cancer cell biomolecules to be achieved, for example, by culturing tumor and/or cancer cells on the substrate. By way of example, the substrate may be further described as a conditioned heterologous, acellular collagenous material. For example, a conditioned heterologous, acellular collagenous material may be prepared from a mammalian tissue, such as an extracellular matrix (ECM) tissue. The tumor and/or cancer cell conditioned substrates, and materials prepared from them, in some aspects may be described as conditioned extracellular matrix materials, wherein tumor and/or cancer cells have deposited and/or excreted cellular biomolecules components, by-products, and/or a complement of other anti-cancer and anti-tumor biomolecules, onto and in the extracellular matrix. In some embodiments, the substrates/extracellular matrix materials may be described as essentially free of viable tumor and/or cancer cells.

In another aspect, a method for inhibiting tumor growth in a patient is provided comprising administering to the patient a composition comprising a tumor and/or cancer mammalian cell conditioned substrate, wherein the substrate is conditioned by culturing tumor and/or cancer cells on the substrate surface under conditions suitable for the growth of the tumor and/or cancer cells. The conditioned substrate will have deposited thereon biomolecules excreted and/or deposited from the culture of mammalian tumor tissue and/or cancer cells. By way of example, it is contemplated that the bioactive materials may include anti-cancer or anti-tumor effective amounts of a combination of 2 or more of: fibrinogen, bFGF, PDGF, TNF-α, endothelins, plasmin or uPA.

In other aspects of the present invention, a method of preparing a composition comprising a mammalian tumor and/or cancer cell conditioned substrate is provided.

In some embodiments, the mammalian tumor tissue comprises a mammalian prostate tumor tissue or prostate tumor cells, or any other tumor cell or population of cells of interest.

In particular embodiments, the prostate tumor tissue is a xenogeneic prostate tumor tissue.

In some embodiments, the conditioned substrate comprises a conditioned heterologous acellular collagenous material preparation, such as a heterologous, acellular collagenous material prepared from an extracellular matrix, that has been processed so as to be essentially free of whole tumor and/or cancer cells. In some embodiments, the tumor and/or cancer cells may be removed from the conditioned extracellular matrix material by a process such as washing, treatment with a chemical agent, sonication or other suitable process that does not destroy and/or significantly affect the structural integrity of the tumor and/or cancer cell conditioned substrate, so as to maintain the integrity of the collagen species (e.g., collagen types I, II, III, and IV) of the conditioned substrate/material. In this state, the processed, conditioned substrate matrix may be described as "decellularized", as defined herein.

In some embodiments, the tumor and/or cancer conditioned substrate material, such as a conditioned heterologous acellular collagenous material, is treated with an agent capable of rendering any tumor and/or cancer cells present on the substrate non-viable and replication incompetent. This may be accomplished using any variety of chemical agents, including, by way of example, potassium thiocyanate, glutaraldehyde, or perhaps a process such as radiation, heat, sonication or other tumor and/or cancer cell disruptive process (e.g., freeze/fracture processing) known to those of skill in the art. Again, any process may be used that does not destroy and/or significantly denature the collagen components of the conditioned substrate material.

In yet other embodiments, the invention provides conditioned substrates that may be used, for example, as wound and/or operative site dressings, particularly at a surgical site where a tumor and/or cancer growth has been removed. For example, a tumor and/or cancer cell conditioned substrate material, such as conditioned heterologous acellular collagenous material prepared from an extracellular matrix, onto which tumor and/or cancer cells have been grown, may be processed as described herein, and used to cover or treat a surgical site on a patient where a tumor growth has been removed. In such embodiments, the conditioned substrates provide a medical graft material having tumor and/or cancer inhibiting properties. In various embodiments, tumor re-growth is inhibited/prevented by use of the conditioned substrates.

In other aspects of the present invention, the anti-tumor/anti-cancer conditioned substrates may be described as comprising a substantially acellular, conditioned extracellular matrix substrate comprising an extracellular matrix material having a surface, and deposited on that surface are biomolecules originating from tumor and/or cancer cells that are non-native to the substrate surface of the extracellular matrix material (i.e., that are added to the surface of the extracellular matrix material, as opposed to being retained from the source of the extracellular matrix material). In certain forms, the inventive composite material is substantially devoid of both tumor and/or cancer cells and tumor and/or cancer cell components, but retains the anti-cancer/anti-tumor substances that have been secreted by the tumor/cancer cells while being cultured on the substrate. In addition, the collagen components of the conditioned substrate are substantially preserved.

In yet other embodiments, injectable preparation forms of the conditioned substrates are provided. In some embodiments, these injectable forms of the anti-tumor/anti-cancer substrates may be formulated so as to be suitable for use as a cancer vaccine. Sterile preparations of particulate preparations of the conditioned heterologous acellular collagenous material substrates may be formulated together with a pharmaceutically acceptable carrier for such product forms.

The terminology used herein is for the purpose of describing particular versions or embodiments only and is not intended to limit the scope of the invention. Unless defined otherwise, all terms of art, notations and other scientific terms or terminology used herein have the same meaning as is commonly understood by one of ordinary skill in the art to which this invention belongs. In some cases, terms with commonly understood meanings are defined herein for clarity and/or for ready reference, and the inclusion of such definitions herein should not necessarily be construed to represent a substantial difference over what is generally understood in the art. However, in case of conflict, the patent specification, including definitions, will prevail.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein.

As used herein, the term "acellular" means free or essentially free from living cells.

The term "decellularizing" or "decellularized" with respect to the description of a material that in its native state includes cells (e.g., a native cell containing ECM material), means that the material is or has been treated to as to remove at least about 70% of the original cells (living or dead). More preferably, at least 80%, 85% or 90% of the cells will be removed, and most preferably at least 99% of the cells will be removed in the decellularization processes involved in the instant invention.

For the purposes of the present invention, the term "heterologous acellular collagenous material" is defined as an acellular, collagenous material that comprises at least one of collagen types I, III, IV, V and V, growth factors, fibronectin, glycoproteins, glycosaminoglycans and laminin, and that is suitable for use as an adjuvant.

The term "patient", as used herein, refers to subjects to be treated including humans and other higher animals, and laboratory models, such as mice and rats.

A "processed" tumor and/or cancer mammalian cell conditioned matrix and/or material, is defined as a substrate, such as a heterologous acellular collagenous tissue preparation (that may in some embodiments of the invention be prepared from a mammalian tissue having an extracellular matrix component), on which tumor and/or cancer mammalian cells have been grown and/or cultured, and then subsequently treated so as to render the tumor and/or cancer cells non-viable and replication incompetent. The conditioned heterologous acellular collagenous tissue preparation may thus be described as a "processed" material. The tumor and/or cancer cell conditioned substrate and/or matrix includes deposited and/or excreted biologically active molecules and metabolic products onto the extracellular matrix.

The term "substantially devoid of cells" means free or essentially free from cells (living or dead). An ECM material substantially devoid of cells is intended to include the ECM material carrying cells at a level sufficiently low to be non-immunogenic when the material is implanted in a recipient, especially a recipient to which the cells are xenogenic or allogenic.

As used in the present application, the term "tumor and/or cancer mammalian cell conditioned matrix" is defined as a cellular matrix on which tumor and/or cancer mammalian cells have been cultured. By way of example, such a matrix may comprise a substrate comprising an extracellular matrix material, such as for example, a SIS substrate. The tumor and/or cancer mammalian cell conditioned matrix is further defined as a processed and/or treated tumor and/or cancer mammalian cell conditioned matrix.

Suitable substrate materials for use in the invention can be provided by heterologous, acellular collagenous material, such as a mammalian tissue material (e.g., ECM materials), including but not limited to those possessing biotropic or remodelable properties, including in certain forms angiogenic collagenous extracellular matrix materials. For example, suitable heterologous collagenous materials include ECM materials such as submucosa, renal capsule membrane, dermal collagen (including processed dermal collagen from human cadavers, which can be used as allograft in humans), dura mater, pericardium, facia lata, serosa, peritoneum, or basement membrane layers, including liver basement membrane. Exemplary submucosa materials for these purposes include, for instance, intestinal submucosa, including small intestinal submucosa, stomach submucosa, urinary bladder submucosa, and uterine submucosa. The preferred medical graft products of the invention will include submucosa, such as submucosa derived from a warm-blooded vertebrate. Mammalian submucosa materials are preferred. In particular, use of submucosa materials derived from animals raised for meat or other product production (e.g., pigs, cattle or sheep) is advantageous. Porcine submucosa provides a particularly preferred material for use in the present invention, especially porcine SIS, more especially porcine small intestine submucosa retaining substantially its native cross-linking.

The submucosa or other ECM substrate material can be derived from any suitable organ or other biological structure, including for example submucosa derived from the alimentary, respiratory, intestinal, urinary or genital tracts of warm-blooded vertebrates. Submucosa useful in the present invention can be obtained by harvesting such tissue sources and delaminating the submucosa from smooth muscle layers, mucosal layers, and/or other layers occurring in the tissue source. For additional information concerning submucosa useful in certain embodiments of the present invention, and its isolation and treatment, reference can be made, for example, to U.S. Pat. Nos. 4,902,508, 5,554,389, 5,993,844, 6,206,931, and 6,099,567, the entireties of which are incorporated herein by reference.

Submucosa or other ECM materials of the present invention can be derived from any suitable organ or other tissue source, especially sources containing connective tissues. The ECM materials processed for use in the invention will typically include abundant collagen, most commonly being constituted of at least about 80% by weight collagen on a dry weight basis. Such naturally-derived ECM materials will for the most part include collagen fibers that are non-randomly oriented, for instance occurring as generally uniaxial or multi-axial but regularly oriented fibers. When processed to retain native bioactive factors, the ECM material can retain these factors interspersed as solids between, upon and/or within the collagen fibers. Particularly desirable naturally-derived ECM materials for use in the invention include significant amounts of interspersed, non-collagenous solids that are readily ascertainable under light microscopic examination. Such non-collagenous solids can constitute a significant percentage of the dry weight of the ECM material in certain inventive embodiments, for example at least about 1%, at least about 3%, and at least about 5% by weight.

As prepared and used, the substrate or other submucosa material or any other ECM material may optionally retain and/or otherwise include growth factors or other bioactive components native to the source tissue. For example, the submucosa or other ECM material may retain one or more growth factors such as basic fibroblast growth factor (FGF-2), transforming growth factor beta (TGF-beta), epidermal growth factor (EGF), and/or platelet derived growth factor (PDGF). As well, submucosa or other ECM material used in certain embodiments of the invention may retain or include other biological materials such as heparin, heparin sulfate, hyaluronic acid, fibronectin and the like. Thus, generally speaking, the submucosa or other ECM material may retain or otherwise include a bioactive component that induces, directly or indirectly, a cellular response such as a change in cell morphology, proliferation, growth, protein or gene expression. In certain preferred embodiments, the ECM material exhibits the capacity to promote angiogenesis.

Further, in addition or as an alternative to the inclusion of such native bioactive components, non-native bioactive components such as those synthetically produced by recombinant technology or other methods, may be incorporated into the submucosa or other ECM material. These non-native bioactive components may be naturally-derived or recombinantly produced proteins that correspond to those natively occurring in the ECM material, but perhaps of a different species (e.g., human proteins applied to collagenous ECMs from other animals, such as pigs). The non-native bioactive components may also be drug substances. Illustrative drug substances that may be incorporated into and/or onto the ECM material can include, for example, antibiotics and/or thrombus-promoting substances such as blood clotting factors (e.g., thrombin, fibrinogen, and the like). These substances may be applied to the ECM material as a premanufactured step, immediately prior to the procedure (e.g., by soaking the material in a solution containing a suitable antibiotic such as cefazolin), or during or after engraftment of the ECM material within the patient.

Submucosa or other ECM material used in certain embodiments of the invention preferably is highly purified, for example, as described in U.S. Pat. No. 6,206,931, which is herein incorporated by reference in its entirety. As such, certain preferred ECM substrate material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example, less than about 1 CFU per gram, more preferably less than about 0.5 CFU per gram. Nucleic acid levels are preferably less than about 5 µg/mg, more preferably less than about 2 µg/mg, and virus levels are preferably less than about 50 plaque forming units (PFU) per gram, more preferably less than about 5 PFU per gram. The ECM material used in certain embodiments of the invention is preferably disinfected with an oxidizing agent, particularly a peracid (e.g., peracetic acid). These and additional properties of submucosa or other ECM materials taught in U.S. Pat. No. 6,206,931, referenced above and incorporated by reference in its entirety, may be characteristic of the submucosa used in certain embodiments of the present invention.

The starting ECM material can optionally include a variety of bioactive or other non-collagenous components including, for example, growth factors, glycoproteins, glycosaminoglycans, proteoglycans, nucleic acids, and lipids. Treating the material with an alkaline substance may reduce the quantity of one, some or all of such non-collagenous components contained within the material. In certain embodiments, controlled treatment with an alkaline substance will be sufficient to create a remodelable collagenous material which is substantially devoid of nucleic acids and lipids, and potentially also of growth factors, glycoproteins, glycosaminoglycans, and proteoglycans. Accordingly, the treatment with an alkaline substance as described herein can cause the material to expand to at least about twice its original volume, can alter the surface and/or porosity characteristics of the material, and can deplete the material of certain bioactive components. In some embodiments, this is accomplished while maintaining the material as an intact collagenous sheet, wherein the sheet can be further processed into any of a variety of the anti-cancer and anti-tumor preparations, such as the cancer vaccine materials, described herein. Further, the remodelable collagenous material, such as an ECM sheet, can be treated with the alkaline medium so as to expand it as described herein, while the material retains an amount of a growth factor such as FGF-2, or another bioactive component such as fibronectin and/or heparin, that is/are native to the source tissue for the ECM or other collagenous material.

In certain embodiments, one or more bioactive components, exogenous or endogenous, for example, similar to those removed from an expanded material during alkaline processing, can be returned to the material. For example, an expanded material can include a collagenous material which has been depleted of nucleic acids and lipids, but which has been replenished with growth factors, glycoproteins, glycosaminoglycans, and/or proteoglycans. These bioactive components can be returned to the material by any suitable method. For instance, in certain forms a tissue extract, such as is discussed in U.S. Pat. No. 6,375,989, which is hereby incorporated herein by reference in its entirety, containing these components can be prepared and applied to an expanded collagenous material. In one embodiment, the expanded collagenous material can be incubated in a tumor and/or cancer tissue and/or tumor cell preparation and/or culture for a sufficient time to allow bioactive components contained therein to associate with the expanded collagenous material. The tumor and/or cancer tissue and/or cell preparation may, for example, be obtained from a tumor tissue of a patient having a particular type of tumor growth type or cancer that the patient will be treated for.

Other means for returning or introducing bioactive components to an expanded remodelable collagenous material include spraying, impregnating, dipping, etc., as known in the art. By way of example, an expanded collagenous material may be modified by the addition of one or more growth factors such as basic fibroblast growth factor (FGF-2), transforming growth factor beta (TGF beta), epidermal growth factor (EGF), platelet derived growth factor (PDGF), and/or cartilage derived growth factor (CDGF). Other biological components may be added to an expanded collagenous material, such as heparin, heparin sulfate, hyaluronic acid, fibronectin and the like. Thus, generally speaking, an expanded collagenous material may include a tumor and/or cancer cell associated bioactive component that induces, directly or indirectly, a cellular response such as a change in cell morphology, proliferation, growth, protein or gene expression.

The preparation of substrate submucosa extracts is described in, for example, U.S. Pat. No. 6,375,989, which is hereby incorporated herein by reference in its entirety. Briefly, a submucosa extract can be prepared by the addition of an extraction excipient, such as urea, guanidine, sodium chloride, magnesium chloride, or a surfactant, to a submucosa tissue to isolate bioactive components from the tissue. The bioactive components are then separated from the extraction excipient. In one preferred embodiment, a submucosa extract is prepared by mixing submucosa tissue with a phosphate buffered solution (e.g., phosphate buffered saline (PBS)). This mixture is processed into a slurry as buffer circulation and physical pressure are applied. The bioactive components present in the tissue are drawn into solution and subsequently isolated from the slurry. The bioactive submucosa extract is then formed by separating the extracted bioactive components in the solution from the slurry using art-recognized procedures (e.g., dialysis and/or chromatographic techniques). Preferably, the extraction solution is dialyzed to reduce or remove the concentration of extraction excipients to provide a solution of the extracted bioactive components. Any source of submucosa tissue can be used to prepare a submucosa extract. Moreover, similar extraction techniques can be applied to other remodelable ECM materials to provide biologically active extracts for use in the invention.

In addition, or as an alternative to the inclusion of native tumor and/or cancer cell and/or cancer tissue bioactive components, such as those provided in a submucosa or other ECM extract, non-native tumor and/or cancer cell/tissue secreted bioactive components including those synthetically produced by recombinant technology or other methods, may be incorporated into the expanded remodelable collagenous material. These non-native tumor and/or cancer cell/tissue secreted bioactive components may be naturally-derived or recombinantly produced proteins, and may correspond to the same or different species (e.g., human tumor and/or cancer cell/tissue secreted proteins applied to collagenous ECMs from other animals, such as pigs). In addition to the non-native tumor and/or cancer cell/tissue secreted bioactive components, it is contemplated that the tumor and/or cancer conditioned substrates may also include drug substances. Illustrative drug substances that may be incorporated into and/or onto the tumor and/or cancer cell conditioned substrate materials used in the invention include, for example, antibiotics, thrombus-promoting substances such as blood clotting factors, e.g. thrombin, fibrinogen, and the like. As with the tumor and/or cancer cell and/or tissue bioactive components previously described, these substances may be applied to the expanded remodelable collagenous material as a premanufactured step, immediately prior to the procedure (e.g., by soaking the material in a solution containing a suitable antibiotic such as cefazolin), or during or after engraftment of the material in the patient.

The substrate extracellular matrix (ECM) base material are preferably naturally-derived collagenous ECMs isolated from suitable animal or human tissue sources. Suitable extracellular matrix materials include, for instance, submucosa (e.g., small intestinal submucosa, stomach submucosa, urinary bladder submucosa, or uterine submucosa, each of these isolated from juvenile or adult animals), renal capsule membrane, amnion, dura mater, pericardium, serosa, peritoneum or basement membrane materials, including liver basement membrane or epithelial basement membrane materials. These materials may be isolated and used as intact natural sheet forms, or particulate form, or reconstituted collagen layers including collagen derived from these materials and/or other collagenous materials may be used. For additional information as to submucosa materials useful in the present invention, and their isolation and treatment, reference can be made to U.S. Pat. Nos. 4,902,508, 5,554,389, 5,733,337, 5,993,844, 6,206,931, 6,099,567, and 6,331,319. Renal capsule membrane can also be obtained from warm-blooded vertebrates, as described more particularly in International Patent Application Ser. No. PCT/US02/20499, published as WO03002165. Each of these references is incorporated by reference herein in its entirety.

Preferred ECM substrate materials contain residual bioactive proteins or other ECM components derived from the tissue source of the materials. For example, they may contain Fibroblast Growth Factor 2 (basic FGF), vascular endothelial growth factor (VEGF), and Transforming Growth Factor-beta (TFG-beta). It is also expected that ECM base materials of the invention may contain additional bioactive components including, for example, one or more of glycosaminoglycans, glycoproteins, proteoglycans, and/or growth factors.

In accordance with one embodiment of the invention, tumor and/or cancer cells will be cultured in vitro on the ECM material under conditions and for a duration of time sufficient to permit secreted tumor and/or cancer cell and/or tissue biomaterials/biomolecules to be deposited upon a portion of or the entire surface of the substrate material, such as to the surface of the ECM material. After deposition of the desired amount of anti-tumor and/or anti-cancer biomolecules into/onto the substrate matrix, the resulting conditioned ECM substrate material can be further processed so as to decellularize the now anti-tumor and/or anti-cancer conditioned substrate. The deposited anti-tumor and/or anti-cancer biomaterials may, for example, also incidentally enhance the functionality of the ECM substrate material, (e.g., by potentially affecting remodeling of the material by non-tumor and/or non-cancer cells present in the patient being treated). In addition, after seeding (e.g., during culture with the tumor and/or cancer cells), the ECM substrate along with the seeded tumor and/or cancer cells can be subjected to mechanical, chemical or physical stresses to influence the cell growth and deposition of tumor and/or cancer deposited products. Such forces could include but are not limited to mechanically stretching the ECM substrate material, preferably without tearing it, subjecting the ECM base material to pulsatile forces (e.g., by flowing fluid such as culture medium through a tube of ECM base material), altering the culture atmosphere (e.g., to a higher or lower carbon dioxide content) or adding specific growth factors or chemokines that affect the cell growth rates, phenotypes, secretory functions or apoptosis events, thereby affecting the molecules deposited by the cells.

Tumor and/or cancer cells to be used to secrete biomolecules into/onto a substrate, such as an ECM substrate, can be applied to the surface of the base ECM supporting structure in any suitable fashion. Illustratively, the tumor and/or cancer cells can be applied to the base ECM material by allowing gravity to settle the cells onto the base ECM. Positive pressure may also be used to force media through the ECM material, thereby depositing cells onto the ECM surface. Other suitable means for applying the tumor and/or cancer cells to the ECM may include, but are not limited to using negative pressure to draw the tumor and/or cancer mammalian cells onto the ECM material, and using chemotactic agents.

In order that the invention disclosed herein may be more efficiently understood, non-limiting examples are provided below. The following examples describe various embodiments of the inventive methods.

Example 1

Materials and Methods

The present example is provided to describe the various materials and methods that were employed in the development and reduction to practice of the present invention.

Methods Animals.

Lobund Wistar (LW) rats were obtained from a breeding colony maintained at the University of Notre Dame. The LW rat is an established model of prostate cancer that metastasizes to the lungs. PAIII cells were originally isolated from an autochthonous, metastatic prostate adenocarcinoma in a LW rat. (Pollard M, Suckow M A. Hormone-refractory prostate cancer in the Lobund-Wistar rat. *Experimental Biology and Medicine,* 230:520-526, 2005). The cells were maintained as tumors by serial passage of tumor samples in LW rats. Typically, these become large subcutaneous tumors weighing in excess of 10 grams. Passage of tumors was performed by harvesting a 5-gram portion of tumor from a euthanized rat and mincing the tissue in 10 ml of Modified Eagle's Medium (MEM). Subcutaneous administration of 0.3 ml of this cell suspension consistently resulted in tumor masses which could be palpated as early as 7 days after cell suspension administration. To create subcutaneous PAIII tumors for this study, rats were administered 0.3 ml of tumor cell suspension subcutaneously over the right flank.

Extracellular Matrix.

Small intestinal submucosa (SIS) (SURGISIS®, Cook Biotech, Inc., West Lafayette, Ind.) was provided as a sterile, lyophilized sheet of extracellular matrix. The SIS was of porcine origin and derived by removal of all mesenteric tissues, serosa, and tunica muscularis from segments of jejunum. Prior to culture with tumor cells and implantation into animals, the SIS was cut into 2 cm×2 cm sections.

Preparation of Vaccines.

Two vaccine preparations were evaluated. One vaccine preparation included a SIS vaccine (SIS/C/L), which consisted of tumor cells harvested directly from a subcutaneous PAIII tumor and which were grown on SIS followed by lysis with potassium thiocyanate. One vaccine preparation comprised SIS on which tumor cells were grown and then fixed in glutaraldehyde (SIS/GFT), also harvested from a subcutaneous PAIII tumor and subsequently fixed in glutaraldehdye. In addition, rats vaccinated with untreated SIS (SIS) and rats vaccinated with SIS which did not have cells grown upon it, but that was subjected to potassium thiocyanate treatment (SIS/L) were included as control groups.

The SIS/GFT vaccine was produced by incubating at 37° C. under 5% $CO_2$, on a 2 cm×2 cm section of SIS in MEM, $1×10^6$ harvested tumor cells. The harvested tumor cells were obtained by harvesting 3 g of a subcutaneous tumor and mechanically dissociating it by fine mincing followed by passage through a 80-mesh screen to create a cell suspension in modified Eagle's medium (MEM) (Suckow, 2005). Following 3 days of growth, SIS with attached cells then underwent incubation in 2.5% glutaraldehdye (v/v) at 37° C. for 60 minutes and was then washed thoroughly with medium to produce the final vaccine preparation. The SIS/C/L vaccine preparation was produced by incubating in MEM $1×10^6$ harvested tumor cells, obtained as for the SIS/GFT vaccine, at 37° C. under 5% $CO_2$ on 2×2 cm sections of SIS. Following 3 days of growth, SIS with attached cells was then placed in 20 ml of 1M KSCN and incubated at 37° C. overnight to lyse the cells. After incubation, the SIS was placed in cold 0.01 M Tris buffer on a stir plate and mixed for approximately 4 hours. After four hours of stirring, the buffer was changed three more times over the next 48 hours. The control SIS which did not undergo cell growth was exposed to KSCN in the same manner (SIS/L). Samples of SIS from each group treated with some form of SIS was fixed in 10% neutral buffered formalin, sectioned, and stained with hematoxylin and eosin to confirm the presence or absence of cells.

Samples were included both for before and after potassium thiocyanate treatment of the SIS that had undergone cell growth, to assure that cells had grown on the SIS and were subsequently removed after thiocyanate treatment.

Surgical Resection of Tumors.

Rats underwent surgical excision of subcutaneous tumors fourteen days after administration of PAIII cells. Following induction of surgical anesthesia with an intraperitoneal dose of ketamine (90 mg/kg) and xylazine (10 mg/kg), the hair overlying the tumor was clipped and the skin scrubbed with an iodophore. Using aseptic technique, tumors were surgically excised and the skin closed with surgical staples. Rats were administered a subcutaneous dose of butorphanol (2 mg/kg) for post-surgical analgesia. With this technique, a small residual tumor bed remains, and tumors typically re-grow within 10-14 days.

Study Design.

To generate subcutaneous PAIII tumors for the present study, 16 male LW rats, 3-4 months old, were administered $1×10^6$ freshly harvested tumor cells subcutaneously in a volume of 0.3 ml of MEM. Fourteen days later, all rats had palpable subcutaneous tumors and underwent surgical resection of the tumors. Rats were then randomly assigned to groups of six, which were treated by placement upon the tumor bed of on of the following: SIS; SIS/L; SIS/GFT; or SIS/C/L. Twenty-one days later, rats were euthanized by carbon dioxide narcosis and the tumors weighed. The differences in the mean tumor weights were evaluated for significance between groups using one-way analysis of variance with significance reached when $p<0.05$.

Histological Examination of SIS Samples.

Samples of SIS/GFT and tumors of rats following resection and vaccination were fixed in 10% neutral buffered formalin. Samples were washed in 70% ethanol and embedded in paraffin, following sectioning at 4-5 μm and staining with hematoxylin and eosin.

Growth of Cells on SIS and Removal by Potassium Thiocyanate Treatment.

Figure 2:
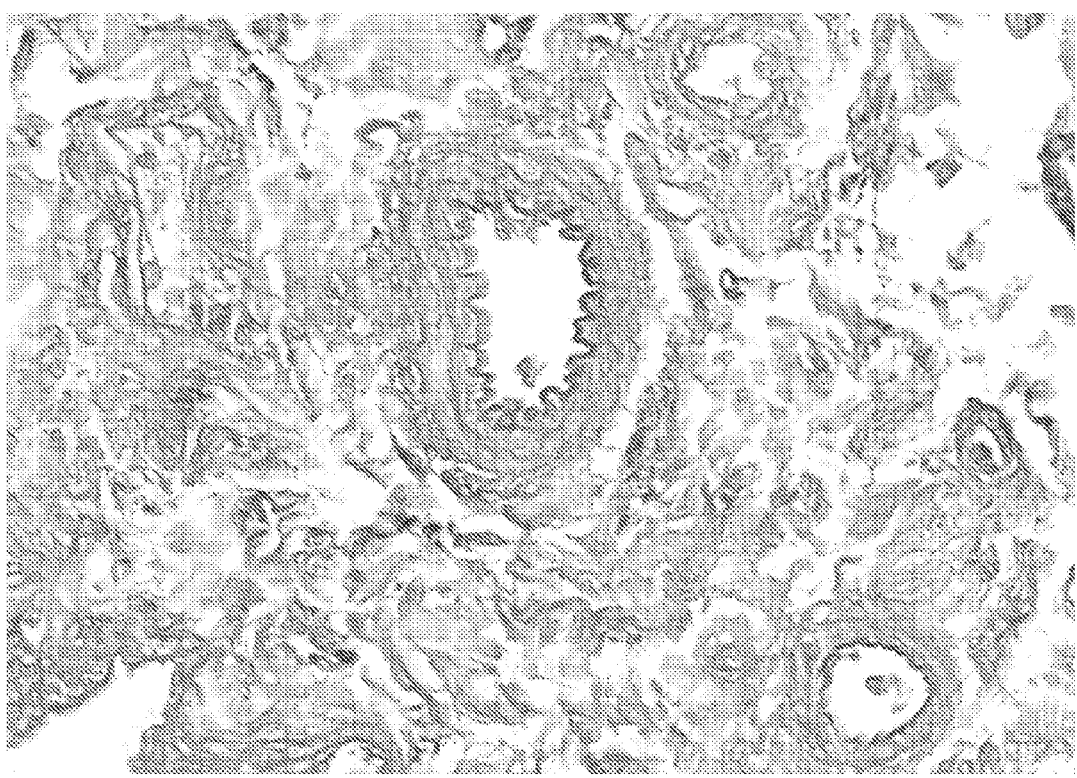
FIG. 2 is a micrograph of tissue, which illustrates that the tumor cells grown on the SIS (as shown in FIG. 1) were removed by potassium thiocyanate treatment, in accordance with one embodiment of the present invention.

As shown in FIGS. 1 and 2, histological examination of SIS samples confirmed that cells grew upon the SIS (FIG. 1) and were subsequently removed by potassium thiocyanate treatment for SIS/C/L (FIG. 2). Samples from the SIS/GFT vaccine confirmed the presence of cells on the SIS, and samples from the SIS and SIS/L groups confirmed the absence of cells upon those materials.

Example 2

In Vivo Anti-Prostate Tumor Activity of Tumor Cell Conditioned Substrate (ECM)

The present example is provided to demonstrate the anti-tumor and/or anti-cancer activity of the present tumor and/or cancer cell conditioned substrates in vivo.

Animals were prepared as described in Example 1. At the time of euthanasia, 21 days after tumor resection and vaccination, tumor weights were as follows:

| Group | Mean tumor wt |
|---|---|
| SIS/C/L | 15.0 |
| SIS/GFT | 14.6 |
| SIS/L | 26.2 |
| SIS | 27.4 |

SIS/C/L = Tumor cells grown on SIS, then lysed with KSCN
SIS/GFT = Tumor cells grown on SIS, then fixed with glutaraldehdye
SIS/L = SIS without cells, treated with KSCN
SIS = SIS without cells, untreated The tumor and/or cancer cell conditioned substrate (ECM) composition stimulated statistically significant (P<0.05) reductions in weight of tumors following tumor resection and vaccination. This response was equivalent to that stimulated by the GFT-S vaccine.

Figure 3:
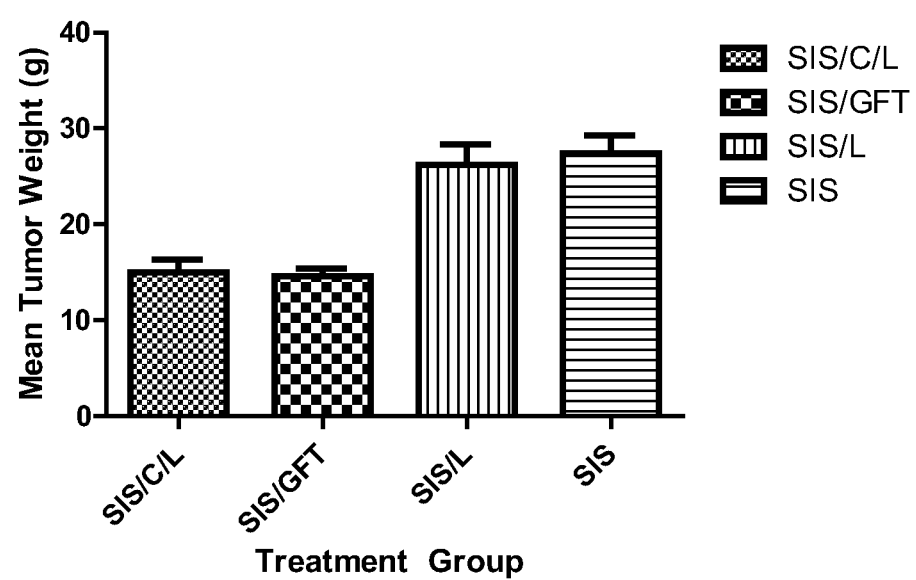
FIG. 3 is a bar chart demonstrating the reduction of tumor re-growth by conditioned extracellular matrix (ECM) media. After tumors were resected and the conditioned media administered, tumors were monitored for re-growth. Bars represent untreated SIS (SIS), SIS treated with potassium thiocyanate (SIS/L), SIS on which tumor cells were grown and then fixed with glutaraldehdye (SIS/GFT), and SIS on which tumor cells were grown and then lysed with potassium thiocyanate (SIS/C/L). Results demonstrate that both SIS/GFT and SIS/C/L vaccination stimulated significant ($P<0.05$) reductions in tumor size. There was no significant ($P<0.05$) difference between tumor size for SIS/GFT and SIS/C/L vaccinated rats.

This data, represented graphically in FIG. 3, demonstrates the utility of the present compositions of SIS-V to stimulate a protective immune response to prostate cancer.

Example 3

Tumor Cell Conditioned ECM Vaccine Study

The present example is provided to demonstrate the utility of the present compositions (e.g., tumor cell conditioned substrates) as anti-tumor compositions.

PAIII prostate adenocarcinoma cells were administered subcutaneously to LW rats to generate tumors. Two weeks after cell administration and once palpable tumors were present, tumors were surgically excised except for a small residual tumor bed. At the time of the surgery, rats were administered a vaccine subcutaneously at a site distant to the tumor bed.

Rats were euthanized 26 days later and the tumors were weighed. (N=4/group; expressed in terms of mean subcutaneous tumor weight).

The conditioned tumor cell substrate vaccine was prepared as described in Example 1. Briefly, tumor tissue as extracted from the rates was cultured on ECM. In one of the vaccine preparations, the culture was treated with potassium thiocyanate. Treatment with the potassium thiocyanate acts to lyse the solid cells grown upon the extracellular matrix material. This provides an essentially cell free (particulate free) preparation. Alternatively, and while not intending to limit the available techniques that may be used remove particulate material from the preparation, one may use potassium thiocyanate, oxycholic acid, freeze-drying the preparation, sonication, etc. It is also envisioned that a protocol of formalin treatment or irradiation would be less favored in the practice of this processing step.

In another vaccine preparation, the tumor cell culture was treated so as to provide a killed tumor cell preparation. This was accomplished by treatment of the tumor and/or cancer cells with glutaraldehdye. In this manner, the tumor and/or cancer cells were not viable, but the tumor and/or cancer cellular antigens of the fixed cells, now replication incompetent, remain in the preparation (the conditioned substrate material (e.g., conditioned ECM)).

The tumor and/or cancer cell-conditioned substrate ECM vaccine that included treatment with a cell lysing composition, such as, by way of example, a thiocyanate (e.g., potassium thiocyanate) performed comparably to the tumor and/or cancer tissue/cell containing preparations prepared from tumor cells treated with a cell fixative agent, such as glutaraldehdye (at least 80-99%, such as 97% of the inhibitory activity). In the preparation where the tumor cells were fixed with glutaraldehyde, fixed cells and cell debris was still present in the medium, while in the potassium thiocyanate treated preparation, the cell debris was essentially eliminated via extensive washing. Thus, it was concluded that the cellular debris as part of the vaccine was not required to elicit anti-tumorigenic properties.

It is envisioned that, while not intending to be limited to any theory or primary mechanism of action, that particulate tumor and/or cancer cell material and/or cell debris was not required as an ingredient of the anti-tumor preparation.

Example 4

Melanoma Inhibition with Tumor Cell Conditioned Substrate (ECM) Vaccine

The present example demonstrates the utility of the present invention for providing a tumor cell conditioned ECM vaccine preparation for use in the inhibition of cancer, such as melanoma. These preparations may be described as essentially free of tumor and/or cancer cell particulate material or whole tumor and/or cancer cells.

Methods.

$1 \times 10^6$ B1 6F10 mouse melanoma cells (American Type Culture Collection, Manassas, Va.) were grown to confluence in modified Eagle's medium (MEM) with added fetal bovine serum. Cells were harvested by mechanical separation from the culture flask. After harvest of cells, the GFT vaccine was prepared by glutaraldehyde fixation, by incubating harvested cells in 2.5% glutaraldehyde (v/v) at 37° C. for 60 minutes, followed by thorough washing with minimal essential media (MEM). To produce the tumor cell conditioned ECM vaccine (TC), B1 6F10 cells were grown on 2×2 cm strips of ECM (SIS) for three days in MEM. Following three days of growth, SIS with attached cells was then placed in 20 ml of 1M KSCN and incubated at 37° C. overnight to lyse the cells. After incubation, the SIS was placed in cold 0.01 M Tris buffer on a stir plate and mixed for approximately 4 hours. After four hours of stirring, the buffer was changed three more times over the next 48 hours. Samples of SIS from each group treated with some form of SIS was fixed in 10% neutral buffered formalin, sectioned, and stained with hematoxylin and eosin to confirm presence or absence of cells.

The vaccination groups were designated as follows:
Control=Minimal essential media (MEM) only
GFT (glutaraldehyde-fixed cultured B16F10 cells) (melanoma tumor cells)
TC (ECM on which B1 6F10 cells were grown and then removed via KSCN lysis and washing)
Two studies were conducted using these vaccines.

Example 5

Treatment of Melanoma

The present example is provided to demonstrate the utility of the present tumor and/or cancer conditioned substrate preparations for inhibiting the growth of melanoma. These tumor and/or cancer preparations are essentially free of particulate tumor and/or cancer whole cells.

Groups of six female C57B16 mice (Harlan, Inc., Indianapolis, Ind.) were administered $1 \times 10^6$ B1 6F10 cells subcutaneously over the left rear flank. Twelve days later, when palpable subcutaneous melanoma tumors were present, mice were vaccinated subcutaneously as a volume of 0.25 ml of MEM; $1 \times 10^6$ GFT melanoma cells (BI6F10 cells) in 0.25 ml of MEM; or a 2×2 cm section of ECM vaccine containing approximately $1 \times 10^6$ GFT cells (TC/ECM).

Animals vaccinated with 2×2 cm sections of SIS were done so via aseptic surgical technique. Briefly, mice were anesthetized with an intraperitoneal dose of ketamine hydrochloride (90 mg/kg) and xylazine (10 mg/kg). After clipping of the hair over the surgical site, a small subcutaneous pocket was surgically created over the dorsal thorax, away from the location of the tumor. The section of ECM was placed within the pocket and the skin closed with surgical glue. Mice were administered a dose (1.0 mg/kg) of butorphanol tartarate for postoperative analgesia. Animals did not receive booster vaccinations. All mice were euthanized 9 days after vaccination and tumors were weighed as a measure of tumor size.

Figure 5:
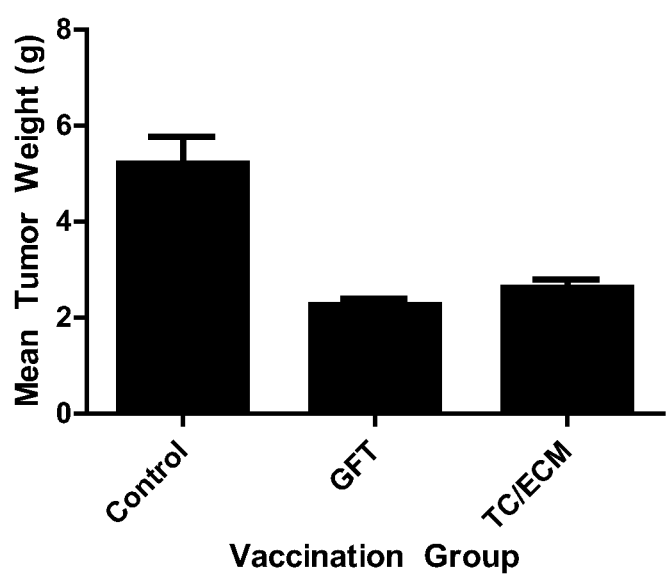

The results from these studies demonstrated that a significant ($P<0.05$) reduction in mean tumor weight was found in the group of mice vaccinated with the GFT vaccine compared to the MEM Control. Further, the TC/ECM vaccine groups showed significant ($P<0.005$) reductions in mean tumor weight compared to the MEM Control groups, and a significant ($P<0.01$) reduction in mean tumor weight compared to the GFT vaccine group (FIG. 5).

These results demonstrate that a conditioned ECM vaccine is an effective treatment for melanoma.

Example 6

Prevention of Tumor Re-Growth After Surgical Debulking

The present example demonstrates the utility of the invention for preventing tumor recurrence after removal of a tumor from a tissue site, such as removal of a tumor growth from a patient.

Groups of six female C57B16 mice (Harlan, Inc., Indianapolis, Ind.) were administered $1 \times 10^6$ B16F10 cells subcutaneously over the left rear flank. Twelve days later, when palpable subcutaneous melanoma tumors were present, the mice underwent surgical tumor debulking. Briefly, the mice were anesthetized with an intraperitoneal dose of ketamine hydrochloride (90 mg/kg) and xylazine (10 mg/kg). After clipping of the hair over the surgical site, the tumor was dissected free of connective tissue attachments and tumor that was visibly discernible was resected.

Vaccines were administered directly onto the tumor bed as a volume of 0.25 ml containing MEM; 0.25 ml of $1 \times 10^6$ GFT melanoma cells in MEM; a 2×2 cm section of TC/ECM vaccine. The skin was closed with surgical glue. Mice were administered a dose (1.0 mg/kg) of butorphanol tartarate for postoperative analgesia.

Seventeen days after tumor debulking and vaccination, the mice were euthanized and the tumors weighed as a measure of tumor size and re-growth.

Figure 4:
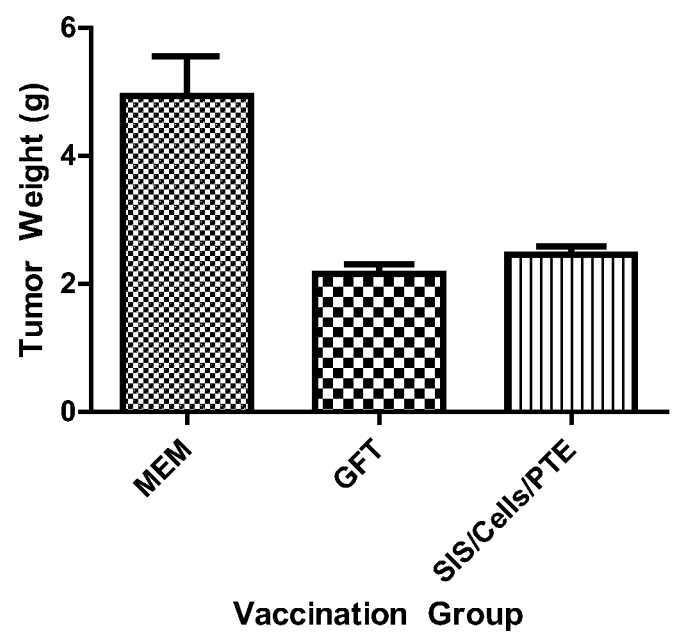
FIG. 4 is a bar chart demonstrating re-growth of melanoma after surgical tumor debulking. Control mice were administered MEM and large tumors quickly regrew. In contrast, there was a significant ($p<0.005$) decrease in tumor size in mice vaccinated with either the GFT vaccine or the TC/ECM (SIS/Cells/PTE) vaccine, indicating that vaccination with either GFT or TC/ECM stimulated protective immunity to re-growth of melanoma. There was no statistically significant difference in tumor size between groups vaccinated with GFT or TC/ECM.

The results are graphically presented in FIG. 4. These results demonstrate that administration of the TC/ECM and GFT vaccines resulted in anti-tumor immunity compared to controls. Mean tumor weights for mice in these vaccination groups were significantly ($P<0.005$) lower than those for the MEM Control group. These results demonstrate that the conditioned ECM vaccine is sufficient to prevent tumor re-growth after surgical tumor debulking.

PROPHETIC EXAMPLE 7

Cancer and Tumor Injectable Vaccines from Conditioned Substrate Material

The present example is provided to demonstrate the anticipated utility of the conditioned extracellular matrix materials found in an injectable formulation for vaccines.

The conditioned preparations of the heterologus acellular collagenous tissue preparations may be pharmaceutically formulated to provide a preparation that may be injected using conventional pharmaceutical techniques, such as via needle injection. Such preparations made by growing tumor cells on particulate ECM, followed by removal of the cells by means such as chemical lysis and washing. Alternatively, tumor cells may be grown on a sheet of ECM, followed by removal of the cells by means such as chemical lysis and washing, with subsequent mechanical disruption of the ECM sheet to form a particulate.

All methods disclosed herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are disclosed herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically disclosed herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

It is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described. It is intended that variations and substitutions for materials specifically identified herein are included within the scope of the present invention.

In addition, it should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

What is claimed is:

1. A pharmaceutical preparation comprising a conditioned heterologous acellular collagenous material on which mammalian tumor tissue or cancer cells have been cultured, wherein said conditioned heterologous acellular collagenous material comprises biomolecules deposited from the culture of the tumor tissue or cancer cells, and wherein the collagenous material has an endotoxin level of less than about 12 endotoxin units per gram.

2. The pharmaceutical preparation of claim 1 wherein the tumor tissue or cancer cells are prostate tumor tissue or prostate tumor cells.

3. The pharmaceutical preparation of claim 1 wherein the tumor tissue or cancer cells are melanoma tumor tissue or melanoma cells.

4. The pharmaceutical preparation of claim 2 wherein the tumor tissue or cancer cells are human prostate tumor tissue or human prostate tumor cells.

5. The pharmaceutical preparation of claim 1 wherein said heterologous acellular collagenous material is an extracellular matrix.

6. A tumor wound dressing material comprising the pharmaceutical preparation of claim 1.

7. An injectable preparation suitable for subcutaneous administration to a patient comprising the pharmaceutical preparation of claim 1 in a particulate form in a pharmaceutically acceptable carrier.

8. The pharmaceutical composition of claim 1 wherein the heterologous acellular collagenous material is derived from small intestinal submucosa.

9. The pharmaceutical composition of claim 1 wherein the heterologous acellular collagenous material is in sheet form.

10. A method for inhibiting tumor growth in a patient comprising applying the pharmaceutical composition of claim 1 to a site at which a tumor or cancerous cell growth has been removed from said patient.

11. A method of preparing a tumor tissue or cancer cell conditioned heterologous acellular collagenous extracellular matrix substrate comprising
    culturing mammalian tumor tissue or cancer cells on a collagenous extracellular matrix substrate to provide a conditioned substrate, and
    removing the tumor tissue or cancer cells from the substrate,
    wherein the conditioned substrate comprises biomolecules deposited from the culture of the tumor tissue or cancer cells, and wherein the collagenous material has an endotoxin level of less than about 12 endotoxin units per gram.

12. The method of claim 11 wherein the tumor tissue or cancer cells are human prostate tumor tissue or human prostate tumor cells.

13. The method of claim 11 wherein the tumor tissue or cancer cells are melanoma tumor tissue or melanoma cells.

14. The method of claim 11, wherein the tumor tissue or cancer cells are removed by treatment of the substrate with a chemical compound.

15. A method for inhibiting tumor growth in a patient comprising
    culturing mammalian tumor tissue or cancer cells on a collagenous extracellular matrix substrate to provide a conditioned substrate, and
    removing the tumor tissue or cancer cells from the substrate to provide a conditioned acellular substrate,
    subcutaneously administering to patient in need thereof the conditioned acellular substrate in a particulate form, wherein the conditioned substrate comprises biomolecules deposited from the culture of the tumor tissue or cancer cells.

16. A method for inhibiting tumor regrowth in a patient comprising
    culturing mammalian tumor tissue or cancer cells on a collagenous extracellular matrix substrate to provide a conditioned substrate, and
    removing the tumor tissue or cancer cells from the substrate to provide a conditioned acellular substrate,
    applying the conditioned acellular substrate to a site at which a tumor or cancerous cell growth has been removed from said patient,
    wherein the conditioned substrate comprises biomolecules deposited from the culture of the tumor tissue or cancer cells.

* * * * *